(12) United States Patent
Edhouse et al.

(10) Patent No.: US 9,017,293 B2
(45) Date of Patent: Apr. 28, 2015

(54) DEVICE FOR AUTOMATIC INJECTION OF DRUG DOSES

(75) Inventors: Mark Jeffrey Edhouse, Cambridge (GB); Philip Jerome Driver, Cambridge (GB); Guy Conwyn Julian Moseley, Waterbeach (GB); Scott Alexander Lewis, Cambridge (GB)

(73) Assignee: Menarini International Operations Luxembourg S.A., Luxembourg (LU)

( * ) Notice: Subject to any disclaimer, the term of this patent is extended or adjusted under 35 U.S.C. 154(b) by 0 days.

(21) Appl. No.: 14/342,754

(22) PCT Filed: Sep. 6, 2012

(86) PCT No.: PCT/EP2012/067438
§ 371 (c)(1),
(2), (4) Date: Mar. 4, 2014

(87) PCT Pub. No.: WO2013/034651
PCT Pub. Date: Mar. 14, 2013

(65) Prior Publication Data
US 2014/0257194 A1    Sep. 11, 2014

(30) Foreign Application Priority Data
Sep. 8, 2011   (IT) .............................. FI2011A0194

(51) Int. Cl.
*A61M 5/32* (2006.01)
*A61M 5/20* (2006.01)
*A61M 5/315* (2006.01)

(52) U.S. Cl.
CPC ............... *A61M 5/3232* (2013.01); *A61M 5/20* (2013.01); *A61M 5/31553* (2013.01);
(Continued)

(58) Field of Classification Search
CPC ......... A61M 5/00; A61M 5/178; A61M 5/20; A61M 5/2033; A61M 5/24; A61M 5/315; A61M 5/31501; A61M 5/31503; A61M 5/31505; A61M 5/31511; A61M 5/31533; A61M 5/31535; A61M 5/31545; A61M 5/31548; A61M 5/3155; A61M 5/31553; A61M 5/3156; A61M 5/3204; A61M 5/3232; A61M 5/3243; A61M 2005/1787; A61M 2005/2013; A61M 2005/202; A61M 2002/2026; A61M 2005/206; A61M 2005/2073; A61M 2005/208; A61M 2005/3247; A61M 2205/581; A61M 2205/582
USPC ......... 604/131, 133, 134, 135, 136, 137, 156, 604/157, 187, 188, 189, 192, 193, 194, 195, 604/196, 197, 198, 208, 209, 210, 211, 220, 604/223, 224, 228, 232
See application file for complete search history.

(56) References Cited

U.S. PATENT DOCUMENTS 4,031,893 A    6/1977 Kaplan et al.
(Continued)

FOREIGN PATENT DOCUMENTS

EP         651662        10/1995
(Continued)

OTHER PUBLICATIONS

PCT International Search Report mailed on Sep. 5, 2011 for PCT/IB2011/050985 filed on Mar. 9, 2011 in the name of Menarini International Operations Luxembourg S.A.
(Continued)

*Primary Examiner* — Bhisma Mehta
*Assistant Examiner* — Nicholas Meghri
(74) *Attorney, Agent, or Firm* — Steinfl & Bruno, LLP

(57) ABSTRACT

A device for the automatic injection of doses of a drug compound is described. The device has a sliding sheath which, when depressed with its front end against the injection site, interacts with cam means to activate triggering of a plunger, thus controlling delivery of a drug dose. Plunger guide means are provided for controlling the triggering sequence and means for arming the device in the dose delivery condition. Automatic needle re-sheathing and resetting of a lock-out condition after each dose is delivered are also provided.

31 Claims, 28 Drawing Sheets

(52) U.S. Cl.
CPC .......... *A61M 5/3156* (2013.01); *A61M 5/3204* (2013.01); *A61M 2005/2013* (2013.01); *A61M 2005/3247* (2013.01); *A61M 2205/581* (2013.01); *A61M 2205/582* (2013.01); *A61M 2005/206* (2013.01); *A61M 5/31535* (2013.01)

(56) References Cited

U.S. PATENT DOCUMENTS

| | | | |
|---|---|---|---|
| 5,665,071 | A | 9/1997 | Wyrick |
| 6,575,939 | B1 | 6/2003 | Brunel |
| 7,396,347 | B2 | 7/2008 | Hjertman et al. |
| 7,597,685 | B2 | 10/2009 | Olson |
| 7,717,877 | B2 | 5/2010 | Lavi et al. |
| 7,976,514 | B2 | 7/2011 | Abry et al. |
| 8,357,125 | B2 | 1/2013 | Grunhut et al. |
| 8,376,993 | B2 | 2/2013 | Cox et al. |
| 2003/0212362 | A1* | 11/2003 | Roser ..................... 604/110 |
| 2011/0034878 | A1* | 2/2011 | Radmer et al. ............. 604/192 |

FOREIGN PATENT DOCUMENTS

| | | | | |
|---|---|---|---|---|
| EP | 0700307 | | 3/1996 | |
| FR | WO 2009/040602 | * | 4/2009 | ............. A61M 5/20 |
| WO | 94/26331 | | 11/1994 | |
| WO | 94/27660 | | 12/1994 | |
| WO | 2009/040602 | | 2/2009 | |

OTHER PUBLICATIONS

PCT Written Opinion mailed on Sep. 5, 2011 for PCT/IB2011/050985 filed on Mar. 9, 2011 in the name of Menarini International Operations Luxembourg S.A.

PCT International Search Report mailed on Dec. 17, 2012 for PCT/EP2012/067438 filed on Sep. 6, 2012 in the name of Menarini International Operations Luxembourg S.A.

PCT Written Opinion mailed on Dec. 17, 2012 for PCT/EP2012/067438 filed on Sep. 6, 2012 in the name of Menarini International Operations Luxembourg S.A.

PCT International Search Report mailed on Dec. 17, 2012 for PCT/EP2012/067431 filed on Sep. 6, 2012 in the name of Menarini International Operations Luxembourg S.A.

PCT Written Opinion mailed on Dec. 17, 2012 for PCT/EP2012/067431 filed on Sep. 6, 2012 in the name of Menarini International Operations Luxembourg S.A.

Notice of Allowance mailed on Oct. 6, 2014 for U.S. Appl. No. 14/342,622 filed on Mar. 4, 2014 in the name of Mark Jeffrey Edhouse et al.

Notice of Allowance mailed on Dec. 18, 2014 for U.S. Appl. No. 13/579,747 filed on Nov. 12, 2012 in the name of Mark Jeffrey Edhouse et al.

* cited by examiner

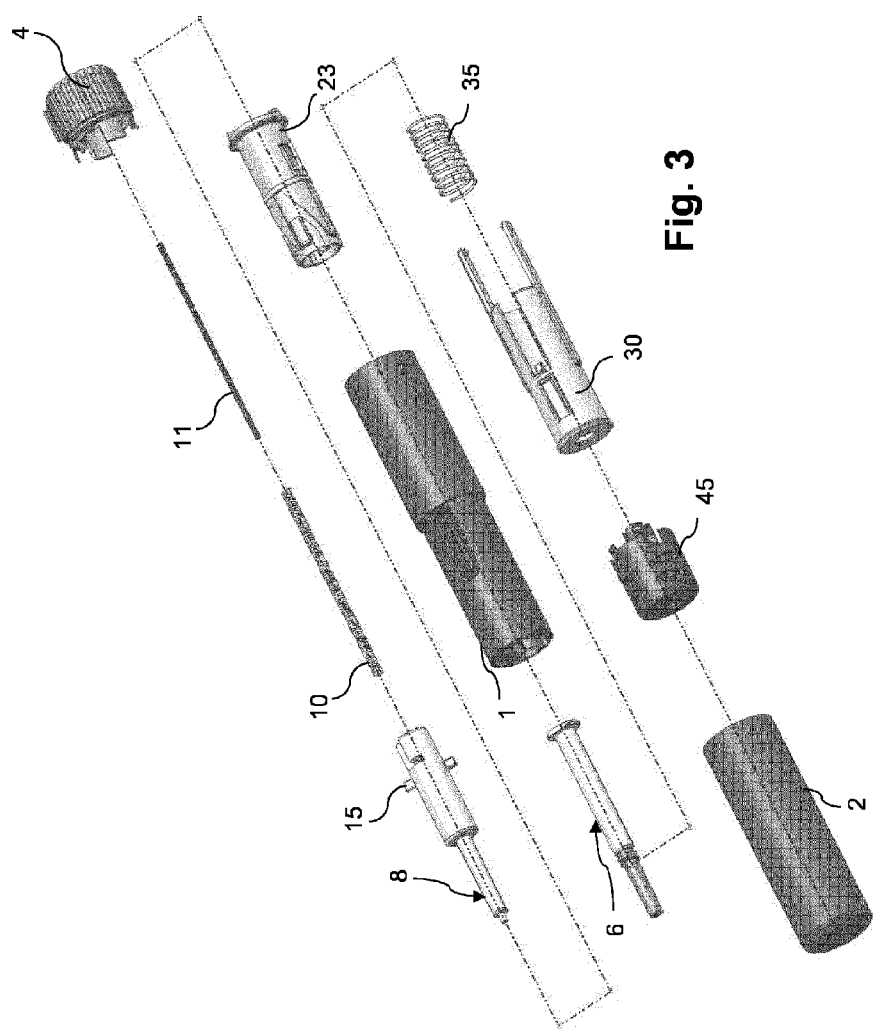

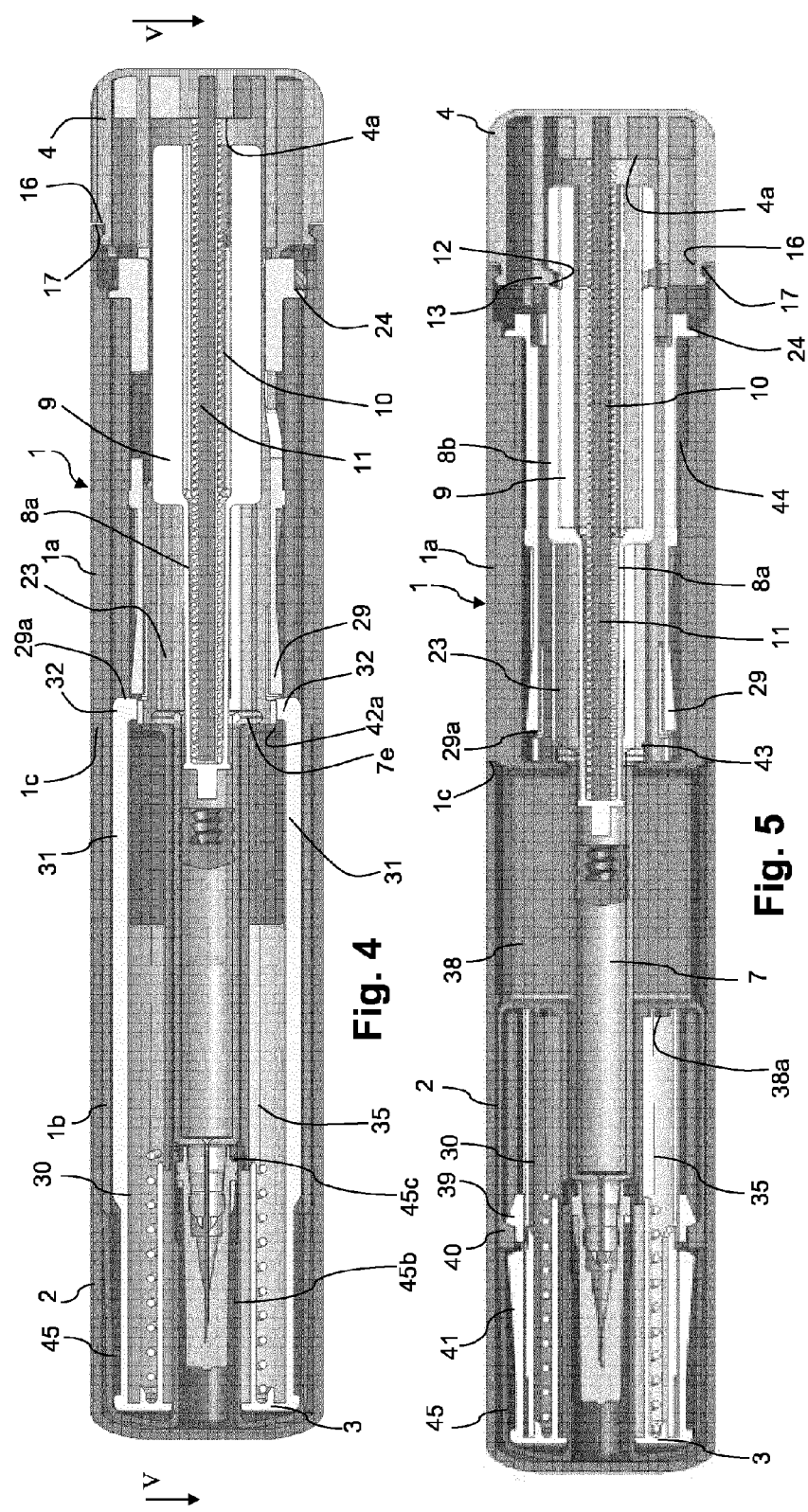

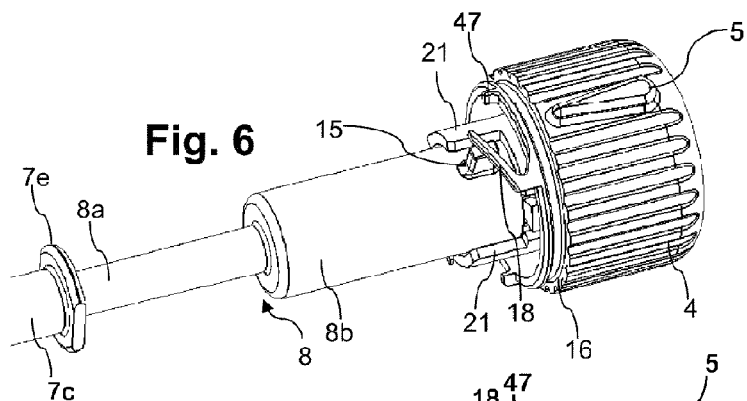
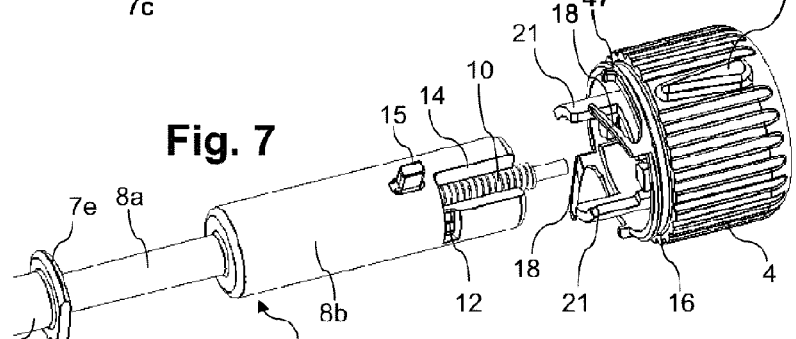
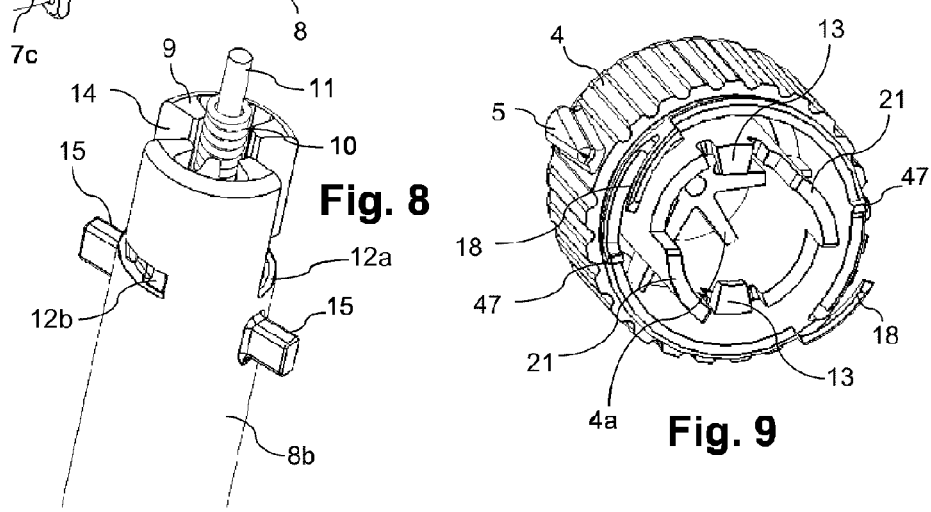

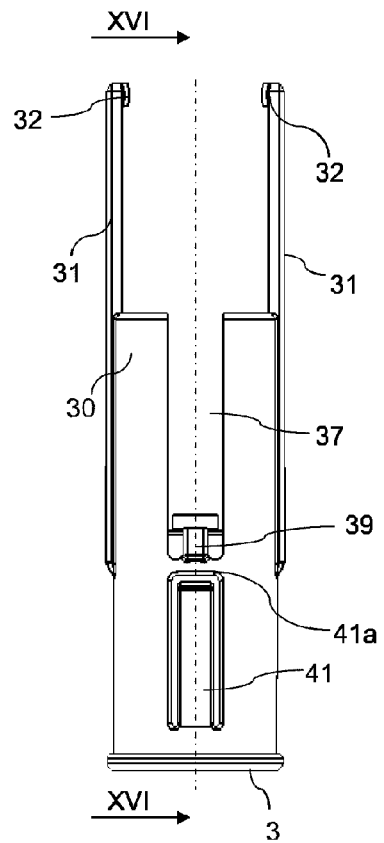
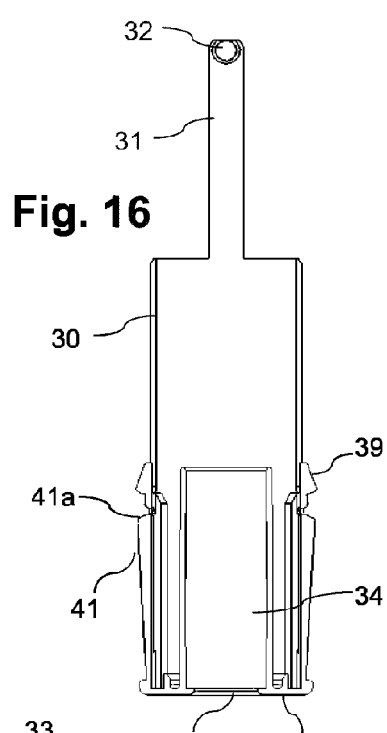
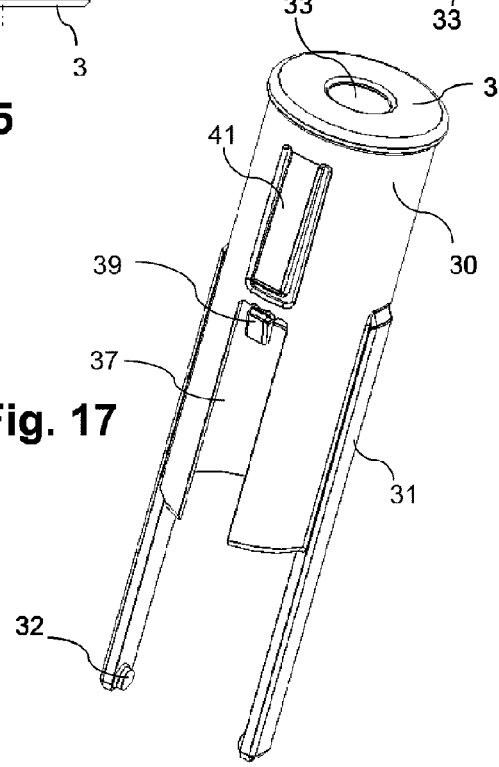
Fig. 15
Fig. 16
Fig. 17

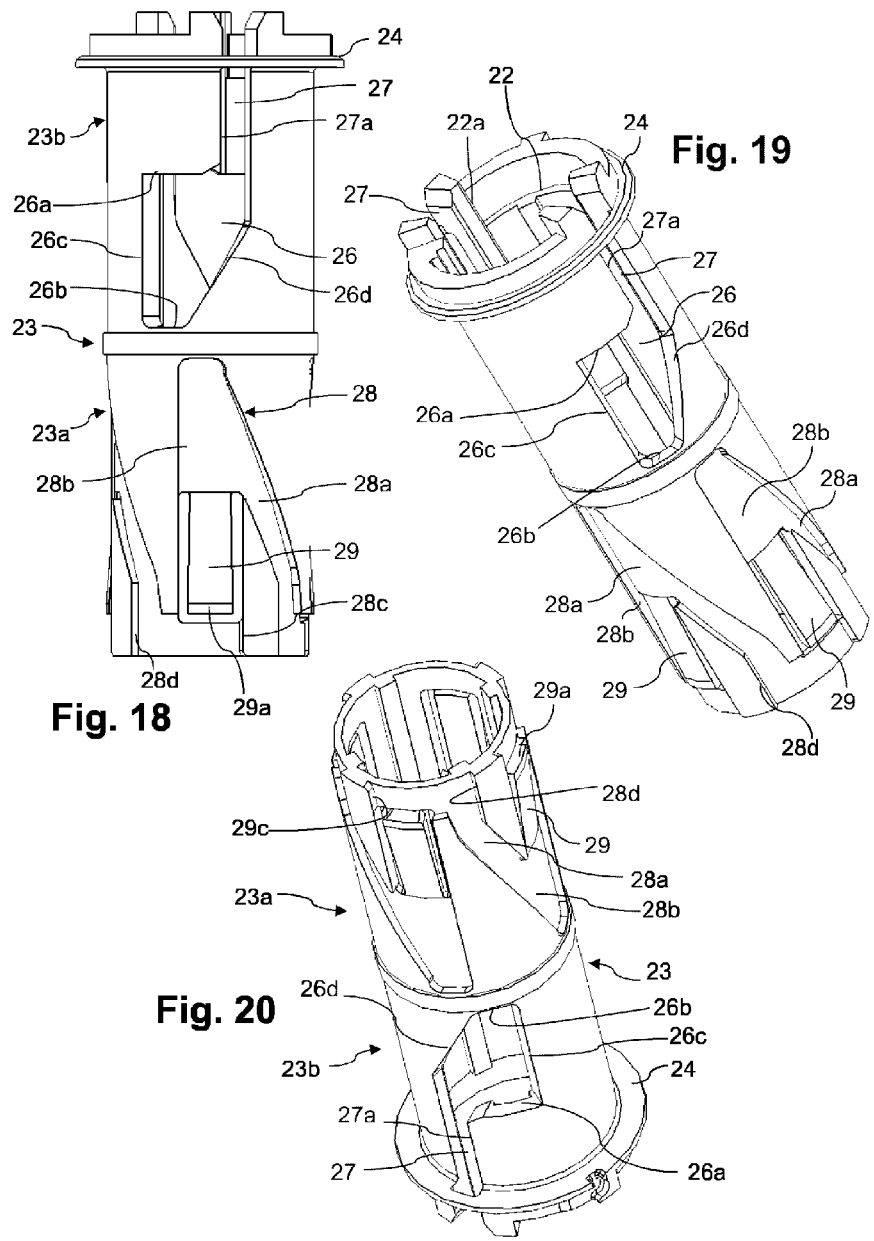

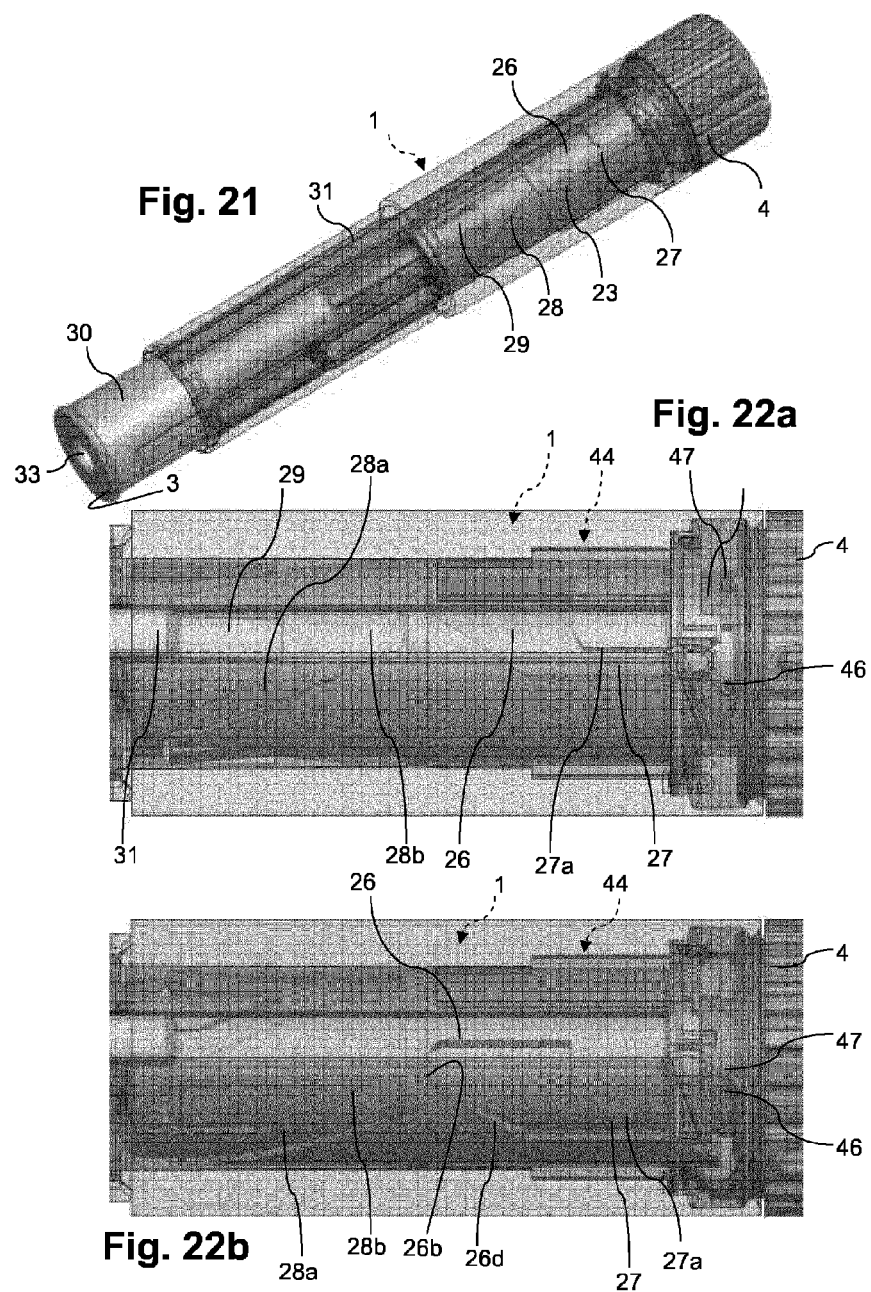

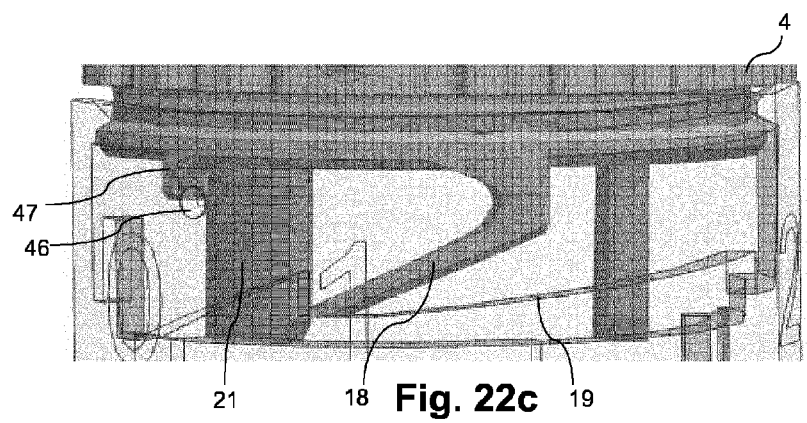
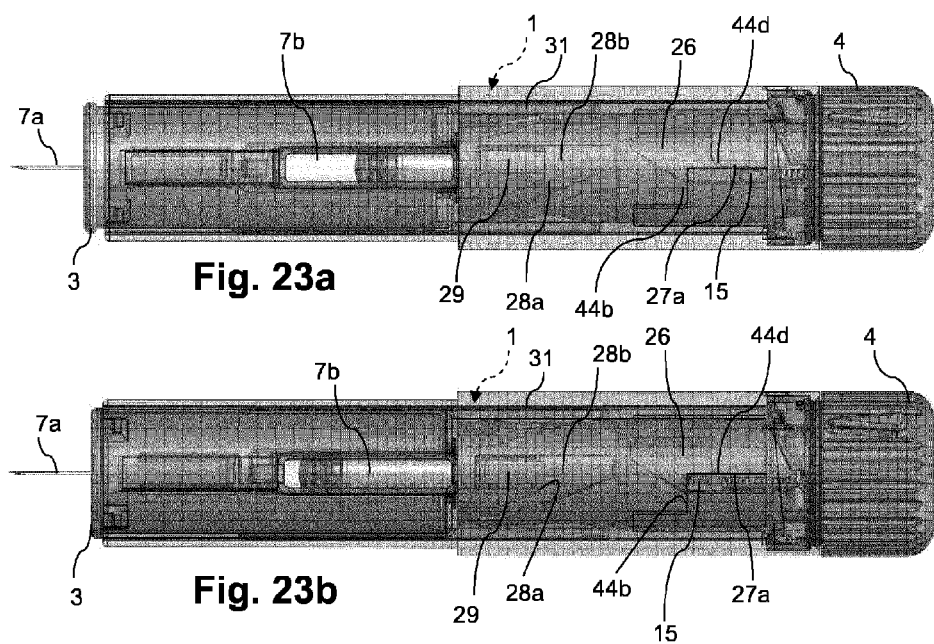

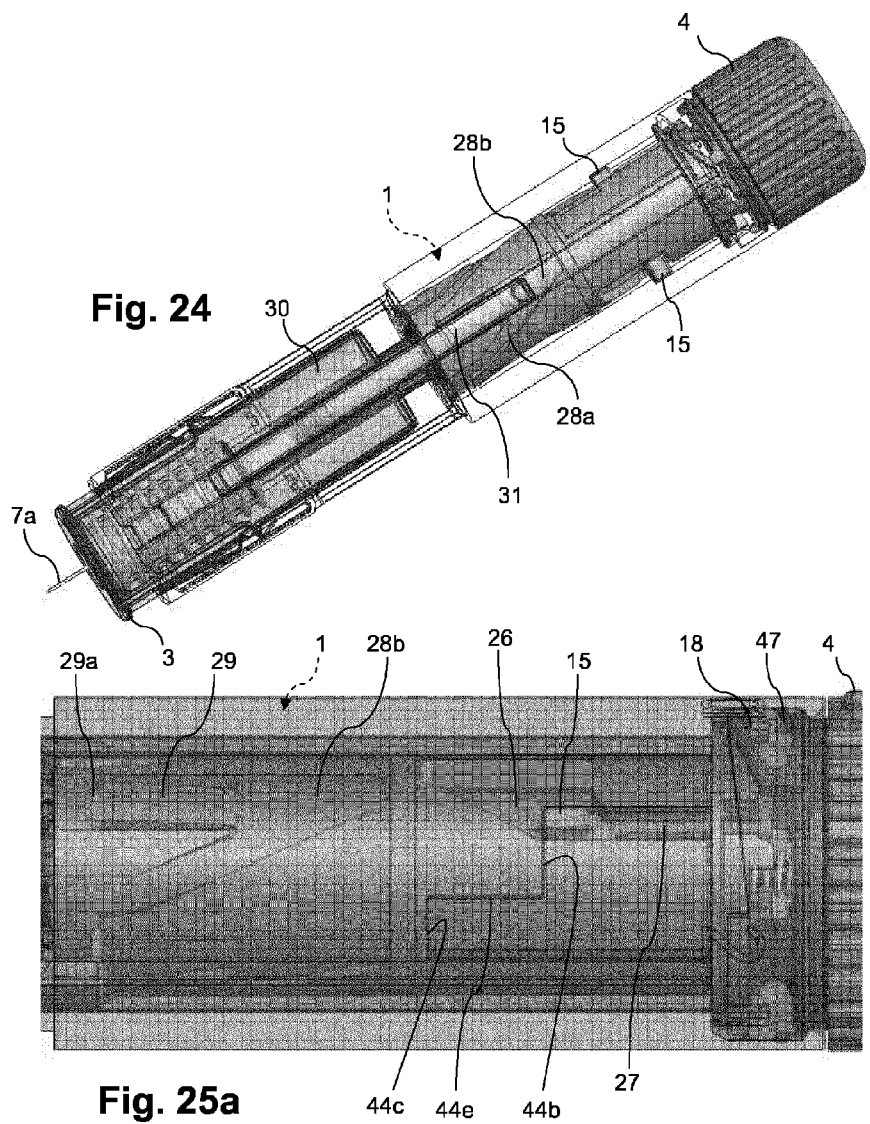

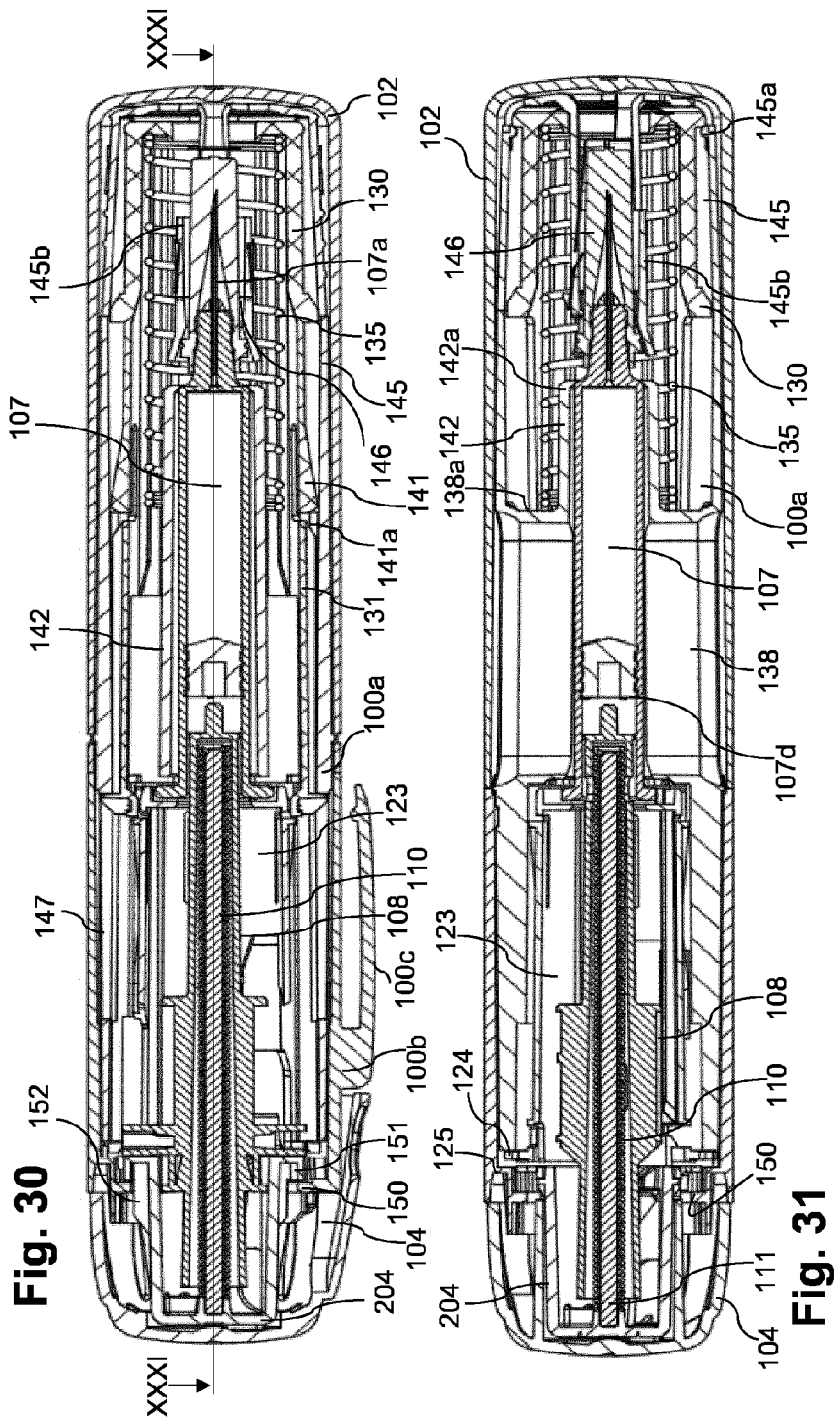

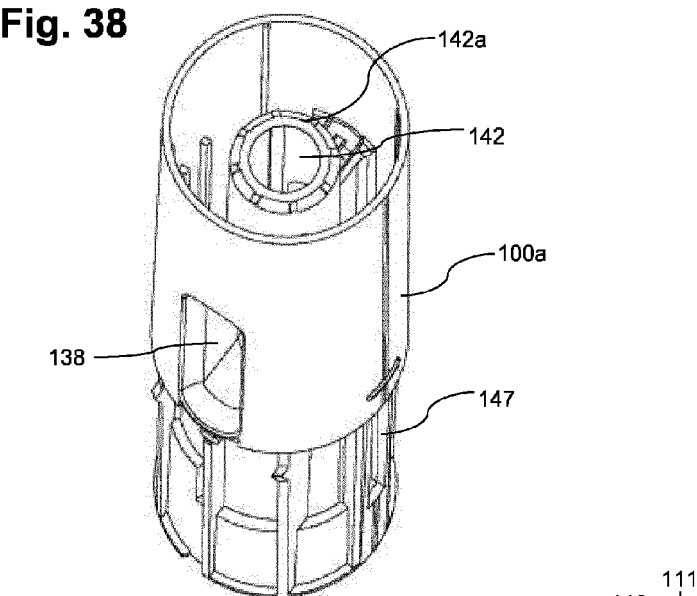
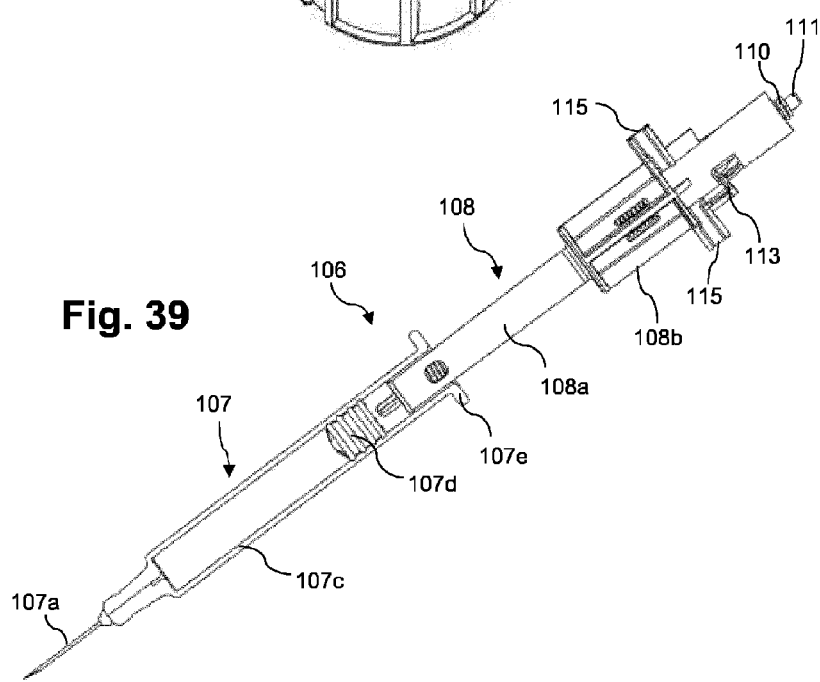

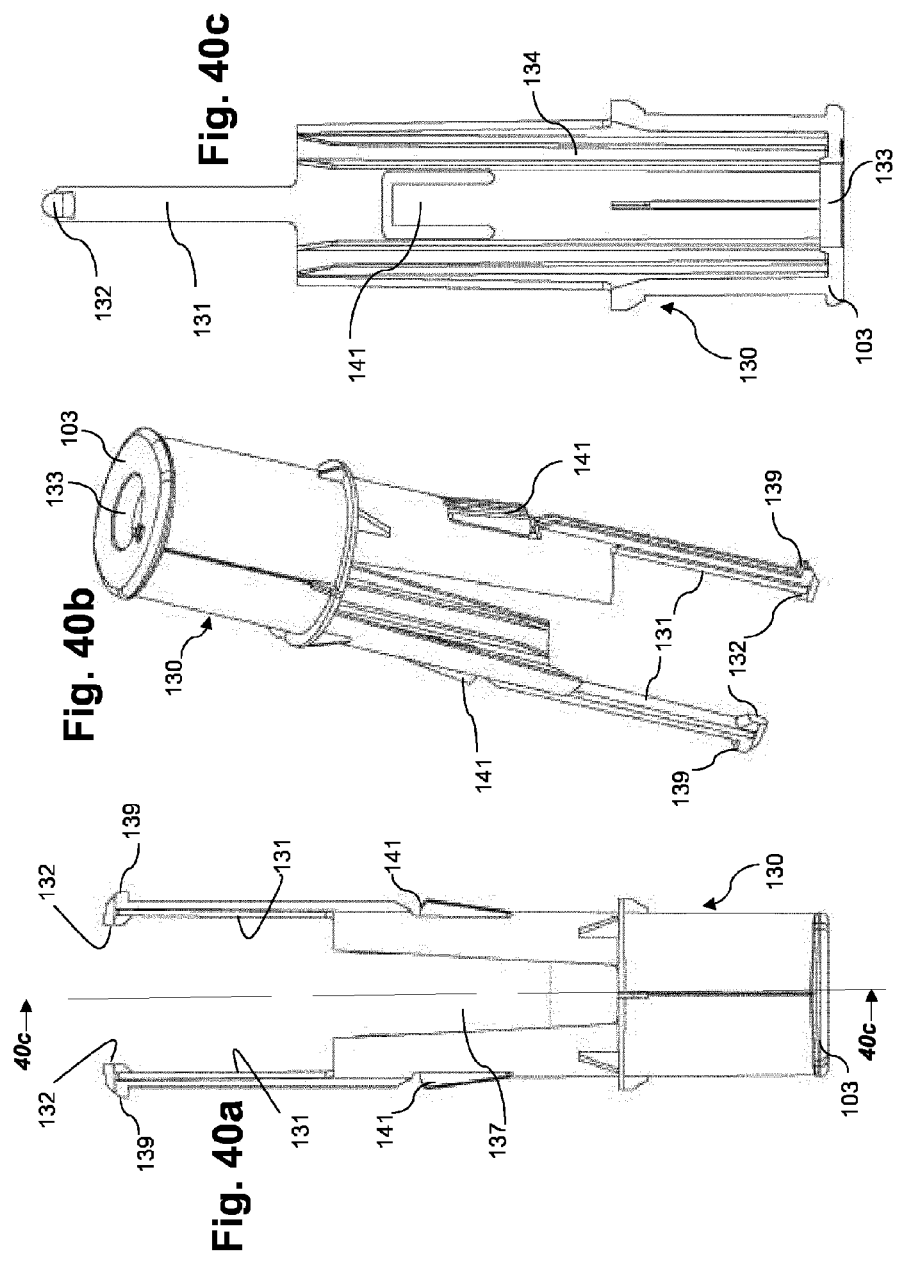

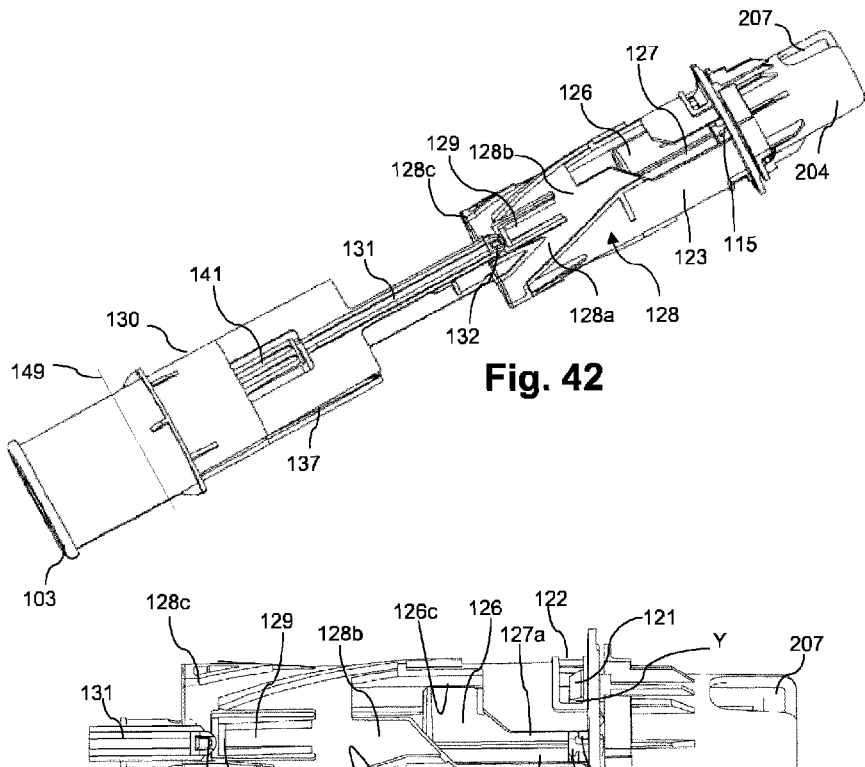
Fig. 42
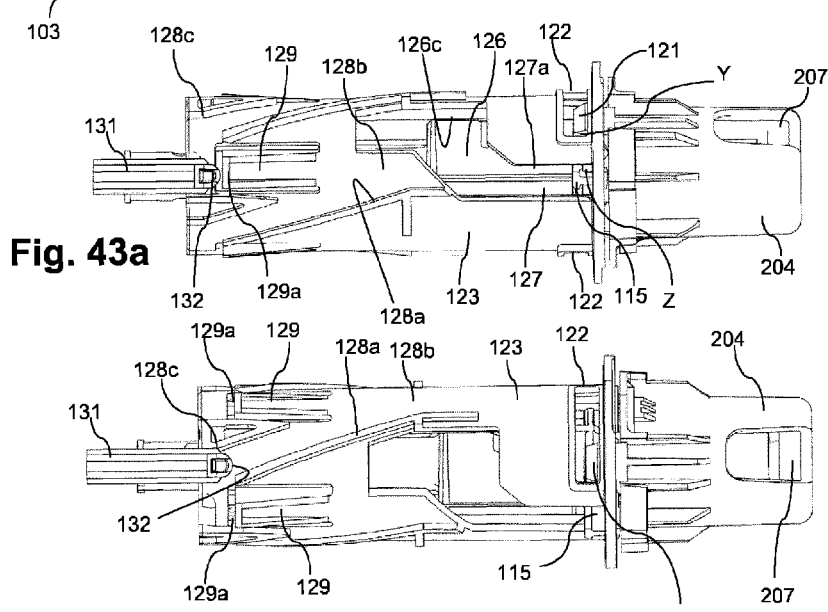
Fig. 43a
Fig. 43b

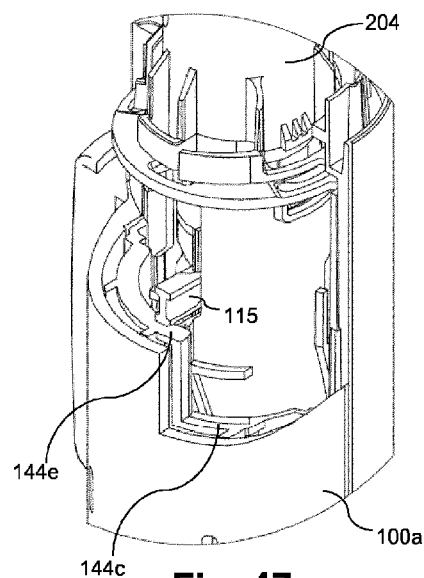 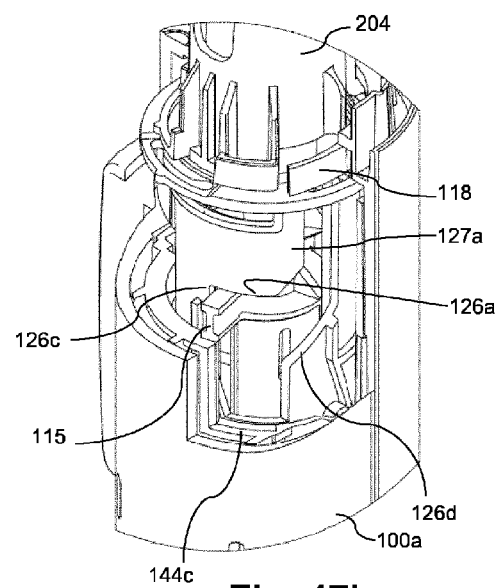
Fig. 47a    Fig. 47b
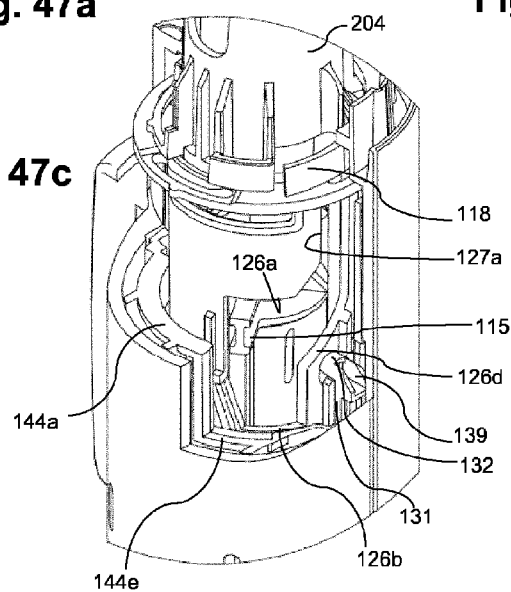
Fig. 47c

DEVICE FOR AUTOMATIC INJECTION OF DRUG DOSES

CROSS REFERENCE TO RELATED APPLICATIONS

The present application is the US national stage of International Patent Application PCT/EP2012/067438 filed on Sep. 6, 2012 which, in turn, claims priority to Italian Patent Application FI2011A000194 filed on Sep. 8, 2011.

FIELD OF THE INVENTION

The present invention relates generally to devices for the injection of medicaments and more precisely relates to a device for the automatic injection of medicaments especially a medicament for allergic emergencies, such as epinephrine or adrenaline, according to a requested time sequence. In particular, the invention refers to a device for the automatic injection of two doses of a medicament at two successive times.

BACKGROUND OF THE INVENTION

Many devices of the above mentioned type allowing a patient to self-administer one or more (generally two) doses of a medicament are known. U.S. Pat. No. 6,575,939 discloses an autoinjector device comprising a syringe housed in a casing formed by an inner part and an outer part capable of sliding in relation to each other. By pressing the end of the inner part (the needle outlet end) against the patient's skin at the injection site, the outer part slides forward along the inner part, thus unlocking a push-button. By depressing the button, the syringe and the relevant plunger are triggered to first thrust in the needle and then deliver the medicament. The needle retraction in the casing is obtained by stopping pressing the outer part end against the skin. This auto-injector allows a single dose of medicament to be administered.

An autoinjector device for automatic administering a single dose of a medicament is also known from U.S. Pat. No. 4,031,893. The autoinjector is equipped with an unlocking device with a deformable member for the driving device. The syringe plunger is axially connected to a rod comprising four flexible axial arms having a toothed end engaged on the edge of an opening formed on a cap placed at the end of the syringe housing. Cap sliding causes the arm ends to deform and their teeth to release from the opening edge. In this way the driving device is triggered. The autoinjector according to this document also comprises a safety device to prevent accidental deformation of the arm ends and triggering of the driving device, consisting of an insert centrally extending from the cap and capable of coming between the rod arms to prevent them from bending.

EP700307 discloses a two-dose autoinjector allowing the automatic delivering of a first dose of a medicament and the manual administration of a second dose. The autoinjector device according to this patent foresees the use of a syringe housed slidably in a tubular housing in two parts that can be separated to allow positioning of the syringe containing two doses of the medicament to be delivered and removal after use. The sliding of the syringe in the housing to penetrate the needle and inject the medicament is operated by an actuator movable between an armed position and an extended position. A releasable locking device is provided to limit the syringe plunger sliding to an extent corresponding to the volume of the first dose. The syringe is mounted in the tubular housing in a movable way to enable the locking device to be removed after the first dose is delivered and the plunger drive means to be armed again, if the second dose is to be automatically administered, or the syringe to be removed, if the second dose is to be manually administered. Furthermore the drive means is provided with a safety lock formed by a member engaging with a deformable pin of the drive means to keep it in a deformed condition, thereby preventing it to trigger. An autoinjector of this type is commercially available under the trade mark Twinject® and allows the first dose to be administered automatically, but the second dose must be manually administered.

The autoinjector according to EP651662 is designed to carry out a sequence of injections from a single syringe that is capable of performing a limited sliding movement in a tubular housing. The syringe has a plunger to deliver doses of a medicine through the needle and spring drive means engage with a plunger rod and, once they are armed, retain the rod in a first position, while, when they are triggered, cause the rod to move forward and this causes first the syringe sliding and needle projection and then a controlled sliding of the plunger to deliver a medicine dose. Manual arming means are provided and means to trigger again the spring drive means.

The plunger rod has a toothed profile on which a catch of the drive means engages and the syringe is housed in a bushing capable of moving in a limited way in the tubular housing and provided with a further catch that is also engaged with the toothed profile of the rod. When the device is armed by the manual arming means, both the drive means and the bushing in which the syringe is placed are displaced toward the rear end of the tubular housing, the two catches engaging with the toothed profile of the rod. An axial groove connection between the bushing and the drive means allows a further sliding between the catch integral to the drive means and the toothed profile of an extent equal to the pitch of the profile. When the device is triggered, first the drive means cause the syringe bushing to slide up to a front stop and then the rod start sliding relative to the bushing catch for an extent corresponding to the profile pitch, whereby the displacement of a volume of medicine is enabled together with its deliver through the needle.

There is a strong need for an injector device for the automatic injection of a medicament in two successive doses which is user-friendly and is easier to manufacture as compared to the conventional devices. The object of the present invention is therefore to meet these requirements by providing a medicament autoinjector device capable of enabling the patient to self-administering two successive doses of a medicament in the easiest possible way, thus sparing the patient of performing potentially dangerous, complex dismounting/rearming operations.

SUMMARY OF THE INVENTION

The general object of the present invention is to provide a device for the automatic injection of multiple discrete nominal volumes of a drug compound, especially two doses of the drug compound from the same syringe.

A particular object of the present invention is to provide a device of the above mentioned type in which the automatic injection of discrete nominal volumes of drug compound is achieved by combination of rotational and translational movements of device components.

Another object of the present invention is to provide a device of the above mentioned type in which the automatic injection of a prescribed dose is triggered by use of a patient activated linear sliding of a component in combination with the angular displacement of plunger means being guided by cam means in an encapsulated chassis.

It is a further object of the present invention to provide a device of the above mentioned type with an automatic sheathing lock-out feature for needle protection and prevention of inadvertent triggering of the device before a dose is selected by the user.

Still another object of the present invention is to provide a device of the above mentioned type capable of automatic re-sheathing the needle and resetting the lock-out condition after a dose is injected.

Another object of the invention is to provide a device of the above mentioned type in which the triggering function and the driving function are integrated on same support to lower tolerances, increase reliability and reduce the number of components of the device, this also resulting in a simple device structure and production cost reduction.

Still another object of the invention is to provide an auto-injector device of the above mentioned type in which the production and assembling thereof are easy to carry out.

The above objects are achieved with the device for the automatic injection of doses of a medicament according to the present invention, whose main features are set forth in the attached claim 1. Further important features are set forth in the dependent claims.

According to an important aspect of the device for the automatic injection of doses of a drug compound according to the present invention, the axial movement of a sliding sheath, caused by the user by depressing its front end against the injection site, causes the angular displacement of cam trigger means, which, in cooperation with stepped guide means, controls the movement of plunger means of a syringe group and thus the delivery of prefixed doses of a drug compound. The movement of the plunger means is produced by axially operating first elastic means, while the axial movement of the sliding sheath is hindered by second elastic means that reinstate the initial needle covering condition of the sheath when the pressure action ceases. To make the device ready for the delivery of a dose, device arming means are provided which, when operated, unlock the sheath axial sliding. The lock-out condition, as well as the needle retraction in the sliding sheath, are automatically reinstated when the pressure ceases under the action of the second elastic means.

According to another important aspect of the invention, the cam trigger means are formed on the same support, axially pivotable, as cam drive means with which the sliding sheath interacts to control the triggering of the plunger means of the syringe group.

According to a further aspect of the invention the means allowing the device to be kept in a rest state are formed on the support of the cam trigger means and the cam drive means and are unlocked as a result of a rotation of a dose selection knob pivotally mounted on the device body and temporarily connected to the support.

BRIEF DESCRIPTION OF THE DRAWINGS

The above and other features, as well as the advantages of the auto-injector device according to the invention will be apparent from the following description of an exemplifying, non-limiting embodiment thereof with reference to the attached drawings, in which:

FIG. 3 is a fully exploded view of the device of FIG. 1;

FIG. 4 is a longitudinal section of the device of FIG. 1;

FIG. 5 is a longitudinal section of the device of FIG. 1 taken along lines V-V of FIG. 4;

FIG. 6 is a detail view of the connection between the dose selection knob and the plunger rod in the device of FIG. 1;

FIG. 7 is an exploded view of the detail of FIG. 6;

FIG. 8 is an axial perspective view of the dose selection knob;

FIG. 9 is a top perspective partial view of the plunger rod;

FIG. 15 is an axial side view of the sliding sheath;

FIG. 16 shows a sectional view of the sliding sheath taken along lines XVI-XVI of FIG. 15;

FIG. 17 is a front perspective view of the sliding sheath of FIGS. 15 and 16;

FIG. 18 is an axial side view of the cam sleeve in the device of the invention;

FIG. 19 is a rear perspective view of the cam sleeve of FIG. 18;

FIG. 20 is a front perspective view of the cam sleeve of FIG. 18;

FIG. 21 shows the device armed for the delivery of the first dose and ready for triggering;

FIGS. 22a, 22b and 22c are detail views of the device of the invention in position 0 (stored position) and in the position 1 (first dose armed);

FIGS. 23a and 23b show the device of the invention at the beginning and at the end of the first dose delivery step;

FIG. 24 shows the device at the resheathing and resetting step;

FIGS. 25a and 25b show the details of the second dose s election step;

FIG. 30 is a longitudinal section of the device of FIG. 27;

FIG. 31 is a longitudinal section of the device of FIG. 27 taken along lines XXXI-XXXI of FIG. 30;

FIG. 38 is a top perspective partial view of the chassis of FIG. 36;

FIG. 39 is an assembly view of the syringe group of the device of FIG. 27;

FIGS. 40 a, b and c are, respectively, side view, perspective view and longitudinal section view taken along lines 40c-40c of FIG. 40a of the sliding sheath in the device of the device of FIG. 27;

FIG. 42 is a perspective view of the operative connection between the cam sleeve and the sliding sheath in the device of FIG. 27;

FIGS. 43a and 43b are detail views of the device of FIG. 27 in position 0 (stored position) and in the position 1 (first dose armed);

FIGS. 47a, b and c are broken-up partial side perspective views showing the device of FIG. 27 at the second dose armed position of FIG. 46b, during the movement toward the triggering point and, respectively at the second dose triggering step;

DETAILED DESCRIPTION OF THE INVENTION

Figure 1:
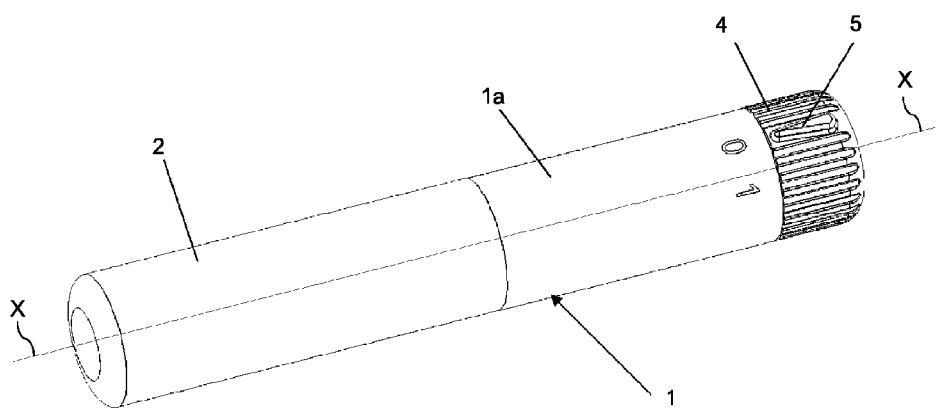
FIG. 1 is a perspective assembly view of the autoinjector device according to the present invention.
Figure 2:
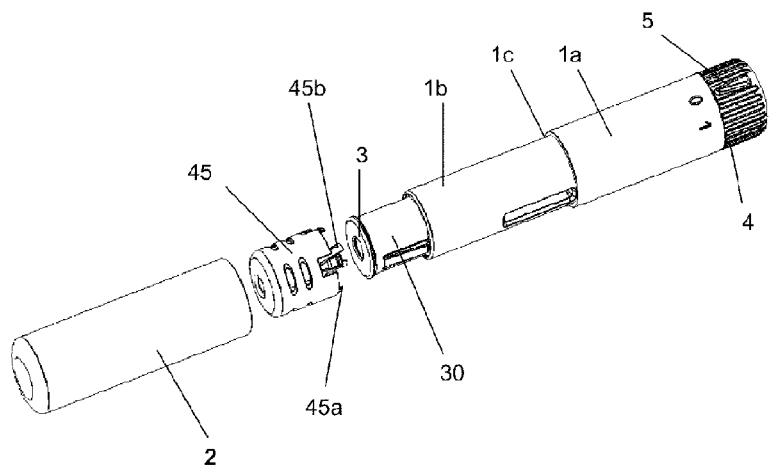
FIG. 2 is a perspective partially exploded view of the device of FIG. 1.

With reference to FIGS. 1 to 5, the autoinjector device according to the present invention comprises an outer body 1 of tubular shape, in particular a cylindrical body, extending along an axis X and containing the majority of the device components. The outer body is formed by two coaxially aligned body portions 1a, 1b having different diameter separated by a step 1c, against which the end of a removable end cap 2 abuts, said cap 2 concealing the front end 3 of the device. In the proximity of the other end, the rear end, of the device angularly spaced reference marks are formed or labelled, for example the numerals 0, 1, 2, indicating a rest o stored state (0), and two operating states (1, 2) of the device, as will be explained later on. In the present description the terms "front", "rear" and equivalents relate to the part of the device intended for the needle outlet and, respectively, the axially opposed part. It is also stated that in the present description reference is always made to a device for the automatic injection of two doses of a drug, but it is understood that the invention also comprises devices capable of delivering more than two doses of a drug at successive times, through changes and alteration to the device which will be obvious for a person skilled in the art.

A dose selection knob 4, on which a reference indicator 5 is formed, is provided at the rear end of the device. The dose selection knob 4 is axially pivotable relative to the outer body 1 to allow the indicator 5 to align to the reference marks 4 formed thereon.

Figure 13:
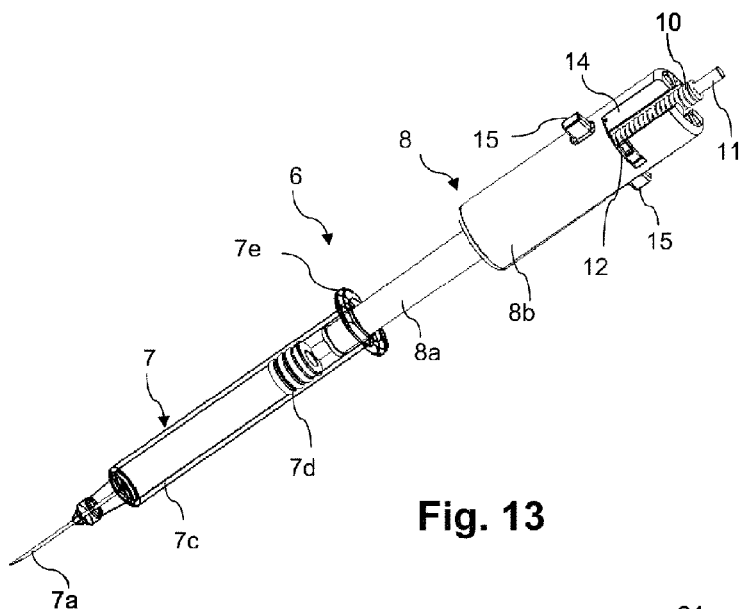
FIG. 13 is an assembly view of the syringe group of the device of the invention.

A syringe group, generally indicated at 6, is housed in the outer body 1. As shown in FIG. 13 the syringe group comprises a drug preloaded syringe 7, with needle 7a, needle shield 7b, barrel 7c and inner plunger stopper 7d. In the barrel 7c there engages the end of a plunger rod 8, formed by a tubular element in two parts 8a and 8b of different diameter. The part 8a has a cross section that is in a clearance condition with respect to the inner section of the barrel 7c so that it can slide therein, and an end shaped in a way to engage with plunger stopper 7d as a result of an axial movement to push it forward on drug delivery. The part 8b of the plunger rod 8 has a larger diameter and is formed with internal radial ribs 9 for aligning a power spring 10 extending axially in the plunger rod 8. The power spring 10 is in a compressed state and abuts against the closed end of the part 8a of the plunger rod 8 with one end and against the bottom wall 4a of the dose selection knob 4 with its other end. The power spring 10 also winds up around a support rod 11 extending from the same bottom wall 4a of the dose selection knob 4 up to the closed end of the part 8a of the plunger rod 8. The arrangement of the power spring 10 between the radial ribs 9 and the part 8a of the plunger rod and the support rod 11 helps to minimize buckling of the power spring 10.

In the device stored state the dose selection knob 4 is connected to part 8b of the plunger rod 8 by a bayonet connection, shown in particular in FIGS. 5 to 9, comprising a pair of substantially L-shaped slots 12 formed circumferentially on part 8b at diametrically opposed positions and a pair of retention clips 13 internally projecting from the dose selection knob 4 at diametrically opposed positions. The substantially L-shaped slots 12 comprise a retention slot branch 12a, extending circumferentially, and a release slot branch 12b, extending axially up to the edge of the part 8b of the plunger rod 8. When the indicator 5 on the knob 4 is aligned to the reference mark 0, the two retention clips 13 are engaged in the respective retention slot branches 12a of the slots 12, thus preventing the plunger rod 8 to slide axially. As a result of an angular displacement of the plunger rod relative to the knob 4, the retention clips 13 slide in the retention slot branches 12a until they come into alignment to respective release slot branches 12b extending rearward up to the free end of part 8b of the plunger rod 8, thereby allowing the plunger rod 8 to travel forward under the action of the power spring 10, as will be explained later on about the device operation.

Two radial pegs 15 outwardly project from the part 8b of the plunger rod at diametrically opposed parts. The two radial pegs 15, which slide in trigger cam means, provide a means to guide the movement of the plunger rod 8 which controls the drug dose delivery, as will be explained later on.

As shown in FIGS. 4, 5 and 6, the dose selection knob 4 is formed with a perimetrical groove 16 in which an undercut 17 at the rear end of the outer body 1 slidably engages, whereby the dose selection knob 4 is pivotable relative to the outer body 1 so that the selection of the dose to be delivered is allowed.

Figure 10:
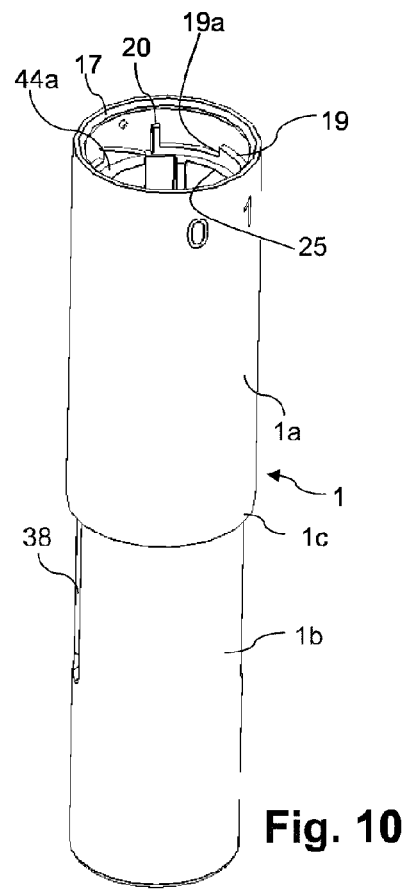
FIG. 10 is a perspective view of the outer body of the device of FIG. 1.

The dose selection knob 4 may rotate in only one direction and to this end the connection between the knob 4 and the outer body 1 comprises means for preventing the rotation in the direction opposite to that of dose selection. These means comprise a pair of ratchet legs 18 (see FIGS. 6 and 7) perimetrically extending from the edge of the knob 4, suited to slidably abut, when the knob 4 is rotated, on an indexing ramp surface 19 defining two ramp steps 19a, b (only one shown in FIGS. 10 and 11). When the legs 18 slide on the ramp surface 19, first they flex and then, once the ramp has overcome, they trigger at the ramp step 19a, b present at the end of the ramp, abutting against it and preventing the reverse rotation. A stop rib 20 is also provided on the ramp surface, against which the ratchet legs 18 abut to prevent any further knob rotation after the knob reaches the position corresponding to the second dose delivery.

As shown in FIGS. 6-8, a pair of diametrically opposed feet 21 axially extend from the free edge of the dose selection knob 4 over the part 8b of the plunger rod 8 and engage in respective seats 22 of a support 23 of tubular shape, referred to as cam sleeve 23 (FIGS. 18 to 20) in the present description, formed at the rear end thereof. The seats 22 have a leading edge 22a against which the feet 21 abut to bring the cam sleeve 23 into rotation integrally with the dose selection knob 4. A positioning flange 24 outwardly extends around the same end of the cam sleeve 23 designed to rest on a corresponding rim 25 within the outer body 1 near its rear end, thereby preventing mutual axial sliding.

Figure 14:
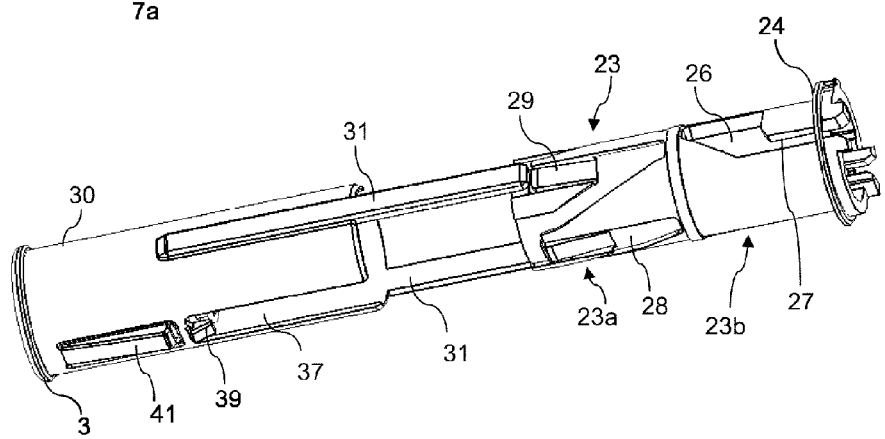
FIG. 14 is a perspective view of the operative connection between the cam sleeve and the sliding sheath in the device of the invention.

As shown in FIGS. 18 to 20, the cam sleeve 23 is formed with two sections with different functions: a first section 23a toward the front end, called front section, and a second section 23b toward the rear end, called rear section. The front section 23a is operatively connected to a slidable sheath 30 (see FIG. 14), whose axial sliding causes the cam sleeve 23 to displace angularly, as will be explained later on, while the rear section 23b is operatively connected to the plunger rod 8 through its radial pegs 15 and, as already said, to the dose selection knob 4 (see especially FIG. 20).

The cam sleeve 23 is pivotable in the outer body 1 and is kept into axial alignment by the positioning flange 24.

The rear section 23b of the cam sleeve 23 is provided with trigger cam means to control the movements of the plunger rod 8. The trigger cam means comprise two windows 26 diametrically opposed and symmetrical to the axial rotation as regard their shape, opened toward the rear edge of the cam sleeve through a respective axially extending channel 27 defining a first dose trigger cam track 27a. Each window is delimited by two parallel circumferential sides 26a, 26b, by an axial side 26c linking two ends of the sides 26a, 26b, and by an inclined side 26d, opposed to the axial side 26c, linking the other end of the side 26b opposite to the channel 27 to one side of the channel 27. The channel 27 opens in the window 26 at the inclined side 26d and the axial side 26c forms the second dose trigger cam track. The first dose trigger cam track 26c is angularly spaced from the second dose trigger cam track 27a.

Drive cam means 28 are embossed on the outer surface of the front section 23a of the cam sleeve 23. The drive cam means 28 is formed by a cam profile repeated four times in an angularly equispaced fashion on said surface. The cam profile comprises a first drive cam track 28a, extending from the end of the sleeve cam 23, called upward track for sake of simplicity, and inclined with respect to the axis X, and a second drive cam track 28b, called downward track for sake of simplicity, extending from the same end of the cam sleeve 23 and incident with the first drive cam track 28a. On the upward track 28a and, successively, on the downward track 28b a pair of drive pins 32 is designed to slide. The drive pins 32 project inwardly from two diametrically opposed, axial drive legs 31 of the sliding sheath 30 (FIGS. 15-17). When a pressure action is exerted on the free end 3 of the sliding sheath 30, the cam sleeve 23 is rotated in the opposite direction to the inclination direction of the upward track 28a, and, respectively, when the pressure action ceases.

In the downward track 28b of the drive cam means 28 relevant cantilever legs 29 are formed to be inwardly deflected to allow passage of the drive pins 32. In the stored state of the device the drive pins 32 abut on an axial lock-out edge 29a (FIGS. 4 and 14) at the free end of the cantilever legs 29, thereby preventing the sliding sheath 30 from moving toward the rear end of the device. A stop edge 28c, placed sideways of the axial lock-out edge 29a, serves as abutment for drive pins 32 to prevent the dose selection knob 4 from rotating beyond the positions of first dose and second dose delivery, as will be explained later on.

The end of the sliding sheath 30 at the side opposite to the drive legs 31 constitutes the front end 3 of the device, i.e. the end intended to be brought into contact with the patient skin at the injection site. The needle 7a of the syringe 7 will project from said front end 3 through a central aperture 33 thereon. A central spring boss 34 for slidably housing the syringe 7 extends from the inner face of the front end 3 of the sliding sheath 30. A return spring 35 is wound around the central spring boss 34 and abuts against the inner face of the front end 3 with one end and against a surface of the outer body 1 with its other end.

The drive legs 31 are slidingly engaged with axial guides 36 formed in the outer body 1, whereby the sliding sheath 30 may only move axially in the outer body 1. Two wide axial openings 37, arranged at 90° relative to drive legs 31, are formed on sliding sheath 30. The axial openings 37 are axially aligned to corresponding transparent inspection windows 38 formed on the outer body 1, through which the barrel 7c of the syringe 7 is visible, whereby the user can control the drug delivery condition. The abutment surface for the return spring 35 on the outer body 1 is constituted by the bottom wall 38a of said inspection windows 38. The axial openings 37 allow the sliding sheath 30 to travel axially by the required distance whilst not clashing with the windows in the outer body 1.

A pair of assembly clips 39 extends from the bottom of, and within the axial openings 37 of the sliding sheath 30 to snap engage with corresponding end stops 40 formed at the front end of the outer body 1, so as to allow the assembly of the sliding sheath 30 within the outer body 1 and prevent release thereof.

The front edge of the outer body 1 abuts on respective lead edges 41a of a pair of flexible tines 41 formed on the sliding sheath 30 at diametrically opposed sides. The lead edge 41a of these tines is inclined so as to provide resistance to the movement of the sliding sheath 30 and make this movement possible only as a result of a moderate thrust that deflects the tines 41 inwardly until the edge of the outer body 1 overcomes the most projecting end of the tines 41. The motion subsequently created by the release of the tines 41 helps to quickly insert the needle 7a of the syringe 7 into the injection site.

A tubular housing 42 for the syringe 7 is formed in the outer body 1 and a flange 42a is formed at one end thereof, on which a corresponding flange 7e of the barrel 7c rests. The two flanges are locked to each other by retention clips 43 inwardly projecting from the outer body 1 (see FIGS. 5, 11 and 13).

Figure 11:
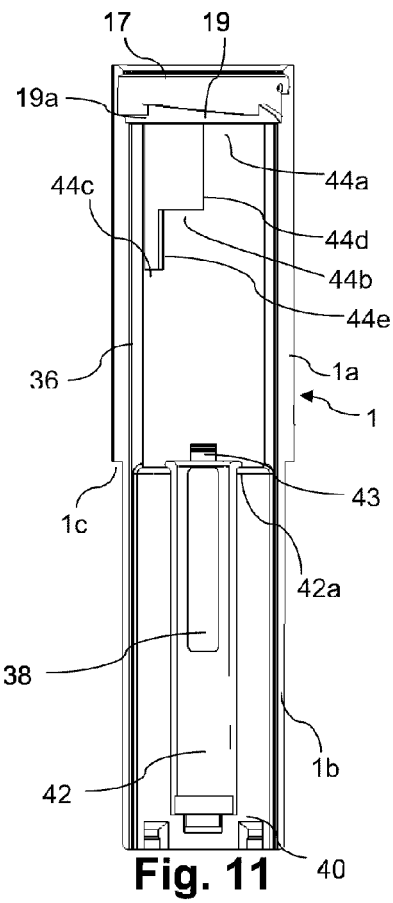
FIG. 11 is a longitudinal section of the outer body of FIG. 10.
Figure 12:
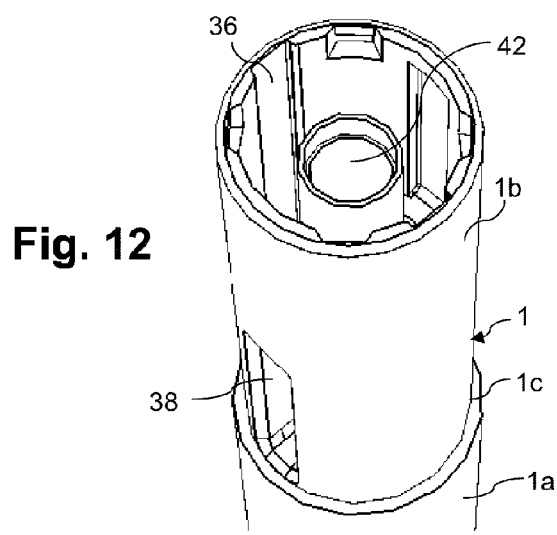
FIG. 12 is a top perspective partial view of the outer body of FIG. 10.

As shown in FIG. 11, guide means 44 are embossed on the inner surface of the outer body 1 to control the axial movement of the plunger rod 8 and limit in this way the volume of delivered drug. These guide means are in the form of a stepped track with a first location face 44a, a second location face 44b and a stop ledge 44c, lying on planes perpendicular to the axis X. The edge of the first location face 44a is connected to the second location face 44b by a first axial side 44d, and the edge of the second location face 44b is connected to the stop ledge 44c by a second axial side 44e. A pair of diametrically opposed stepped tracks, symmetrical to the axial rotation as regards their shape, are formed in the outer body 1. The radial pegs 15 of the plunger rod 8 are designed to slide along the first and the second location faces 44a and 44b as a result of the rotation of the cam sleeve 23 and fall off from the first location face 44a to the second location face 44b and from the latter to the stop ledge 44c on delivering the first and the second dose of drug, while moving along the first axial side 44*d* and, respectively, the second axial side 44*e*, as will be explained later on.

A needle shield remover 45 (FIGS. 2 to 5) is removably secured to the outer body 1 by snap engageable retention fingers 45*a* and is provided with an inner tubular grip 45*b* fit for engaging with the needle shield 7*b*, in such a way that, by pulling the needle shield remover 45 before the first dose is administered, the user can remove the needle shield 7*b* and free the needle 7*a* for the injection.

The following is a description of the way the auto-injector device according to the invention is used.

In the initial state, the stored state, the power spring 10 is compressed between the closed end of the part 8*a* of the plunger rod 8 and the bottom wall 4*a* of the dose selection knob 4. The bayonet connection between the knob 4 and the plunger rod 8 secures the power spring 10 in compression until the first dose is selected. Any buckling of the power spring 10 is prevented thanks to its being arranged between the radial ribs 9 and the part 8*a* of the plunger rod 8 at one side and the support rod 11 at the other one. The needle shield 7*b* is secured to the syringe 7 and the needle shield remover 45 secured to the needle shield 7*b*. The cap 2 is secured to the outer body 1 and the sliding sheath 30 is prevented from moving axially because the drive pins 32 of the of the drive legs 31 abut against the respective lock-out edges 29*a* of the cam sleeve 23.

The dose selection knob 4 is connected to the outer body 1 through its external perimetrical groove 16, with which slidingly engages the undercut 17 on the rear end of the outer body 1. Once assembled, the dose selection knob 4 cannot move axially, but can only rotate in one direction. The rotation direction is indicated by the reference marks on the outer body: in other words, indicator 5 starts from the position 1, rotates to the position 1 when the first dose is selected, and then rotates to the position 2 when the second dose is selected.

In the stored state the device is "locked-out", i.e. the sliding sheath 30 cannot move in the outer body 1, because the drive legs 31 of the sliding sheath 30 abut against the axial lock-out edges 29*a* of the cam sleeve 23. This condition is shown in particular in FIG. 14. On selecting the first dose (position 1), the device is unlocked as shown in FIG. 21. As a matter of fact, by rotating the dose selection knob 4 the cam sleeve 23 is pushed in the same direction by the feet 21 of the knob 4 that abut on the leading edge 22*a* of the seats 22 of the cam sleeve 23. The dose selection knob 4 cannot rotate past the position 1 until the first dose is delivered, because the drive pins 32 of the legs 31 abut on the circumferential stop edge 28*d* of the cam track 28 on the cam sleeve 23. The slidable sheath 30 is prevented from rotating because the legs 31 can only move axially forward and backward in the axial guides 36 on the outer body 1.

First the user must slide back and remove the end cap 2 in order to expose the needle shield remover 45. The end cap 2 will have to be replaced once the first dose is delivered when the device is not in use. The end cap 2 protects the drug from light exposure and prevent particulates from coming into contact with the front end 3 of the device.

To perform the first injection the user must remove the needle shield remover 45. In this way the needle shield 7*b* is also removed leaving the needle 7*a* uncovered, but still subflush of the front end 3 and not readily visible to the user. To unlock the device and select the delivery of the first dose, the user rotates the dose selection knob 4 from position 0 (stored state) to position 1 (first dose armed).

The rotation of the dose selection knob 4 from position 0 to position 1 causes the rotation of the cam sleeve 23, whereby the axial lock-out edges 29*a* of the cantilever legs 29 displace relative to the drive pins 32 of the legs 31 of the slidable sheath 30, which abut against the circumferential stop edge 28*d* to prevent the knob 4 to further rotate until the first dose is delivered and are aligned to the upward portions 28*a* of the cam track 28 free to move along them. The user recognizes the end of rotation to position 1 when he/she sees that the indicator 5 lines up with the position 1 marker, feels the increase in rotation resistance of the drive pins 32 contacting the cam track 28 and also hears the "click" as produced by the ratchet legs 18 falling off the step 19*a* of the ramp surface 19. The contrast between legs 18 and steps 19*a* prevent the knob 4 from rotating in the reverse direction.

The device is triggered by the user pressing the front end 3 of the sliding sheath 30 against the injection site by keeping the device through the outer body 1. The movement of the sliding sheath 30 in the outer body 1 finds a resistance due to the contrast between the flexible tines 41 and the end of the outer body 1. Due to their flexibility and the inclined contact surface, the flexible tines 41 depress and fully deflect inwardly to allow the passage of the sliding sheath 30 which can slide in the outer body 1 leaving the needle 7*a* to project from its front end 3, so that the needle can penetrate in the injection site. The motion subsequently created by the release of the flexible tines 41 helps to quickly insertion of the needle 7*a* in the injection site.

The axial movement of the sliding sheath 30 in the outer body 1 causes the rotation of the cam sleeve 23 and the latter would frictionally draw into rotation also the dose selection knob 4. To prevent the knob 4 from rotating during the step of first dose delivery, between the dose selection knob 4 and the outer body 1 temporary stop means are provided that mutually engage when the free ends of the ratchet legs 18 fall off the step 19*a* of the ramp surface 19 of the outer body 1. In the present embodiment the temporary stop means comprise retention pips 46 of the outer body engaging with corresponding catches 47 of the knob 4, as shown in FIGS. 6, 11 and 22*c*. The rotational force acting on the dose selection knob 4 upon triggering is less than the retention force provided by the pips 46. However, the rotational force that the user is able to provide is much larger than that of pips. Therefore, the user can overcome the pip force and rotate the knob 4 to arm the device for the second dose.

The rotation of the cam sleeve 23 causes the plunger rod 8 to rotate because of the engagement of its radial pegs 15 in the corresponding axial channels 27. After a few degrees of rotation the bayonet connection between the dose selection knob 4 and the plunger rod 8 decouples because the retention clips 13 of the knob 4 reach the relevant axial release slot branches 12*b* of the plunger rod 8 and, under the action of the power spring 10, the plunger rod 8 is pushed forward to bring the radial pegs 15 to lean on the first location face 44*a* of the stepped guide 44 of the outer body 1.

While the cam sleeve 23 keeps rotating, the radial pegs, pushed by the first dose trigger cam track 27*a*, slide on the first location face 44*a* until they reach the end thereof and fall off the second location face 44*b* of the stepped guide 44 under the action of the power spring 10. This sequence is shown in FIGS. 23*a* and 23*b*. The resulting axial sliding of the plunger rod 8 causes the delivery of the first dose.

After delivery of the first dose, the user removes the device from the injection site and the needle 7*a* withdraws therefrom. The return spring 35 is no longer hindered by the forced contact between the front end 3 and the injection site and thereby pushes the slidable sheath 30 axially forward thus resheathing the needle. At the same time the drive pins 32 of the drive legs 31 slide down in the downward portion 28*b* of the cam track 28 depressing inwardly the cantilever legs 29 until the device returns to a "lock-out" condition, wherein the drive pins 32 contact the free end 29a of the cantilever legs 29 and the assembly clips 39 of the sliding sheath 30 again engage with end stops 40 of the outer body 1, as shown in FIG. 24. The needle 7a is again not accessible as being covered by the sliding sheath 30, which, in this state, is prevented from sliding until the user rotates the dose selection knob 4 to position 2. The user then recaps the device. The end cap 2 snap fits with outer body 1 to securely hold on the device.

If the delivery of a second dose is necessary, the user un-caps the device to enable access to the sliding sheath 30. To unlock the device the user must rotate the dose selection knob 4 from the position 1 (first dose armed position) to the position 2 (second dose armed position).

To that end the user must overcome the reaction of the catches 47 of the knob 4 on retention pips 46 of the outer body 1. The feet 21 of the knob 4 take up the free travel on seat 22 of the cam sleeve 23 until they reach the leading edge 22a to rotate the cam sleeve 23 to position 2, as shown in FIGS. 25a and 25b. At the same time the rotation of the cam sleeve 30 causes the device to unlock because the drive pins 32 of the drive legs 31 of the sliding sheath 30 line up the upward portion 28a of the cam track 28 while contacting the circumferential stop edge 28d to prevent a further rotation of the knob 4 once the position 2 is reached. The reverse rotation of the dose selection knob 4 is prevented by the ratchet legs 18 snap abutting on step 19a of the ramp surface 19. The rotation of the cam sleeve 23 also causes the repositioning of the radial pegs 15 from the outlet of the axial channel 27 within the window 26 to the opposite axial side 26c, while their position on the second location face 44b of the stepped guide 44 is unchanged.

The device is triggered for the delivery of the second dose by the user pressing the front end 3 of the sliding sheath 30 against the injection site by keeping the device through the outer body 1. The movement of the sliding sheath 30 in the outer body 1 finds a resistance due to the contrast between the flexible tines 41 and the end of the outer body 1. Due to their flexibility and the inclined contact surface, the flexible tines 41 depress and fully deflect inwardly to allow the passage of the sliding sheath 30 which can slide in the outer body 1 leaving the needle 7a to project from its front end 3, so that the needle can penetrate in the injection site. The motion subsequently created by the release of the flexible tines 41 helps to quickly insert the needle 7a in the injection site.

To prevent any further rotation of the knob 4, once the position 2 is reached, at the end of the following rotation of the cam sleeve 23 the base of the ratchet legs 18 contacts the stop rib 20 of the indexing ramp 19, by what the ratchet legs 19 are retained between the step 19a and said stop rib 20.

Figure 26A:
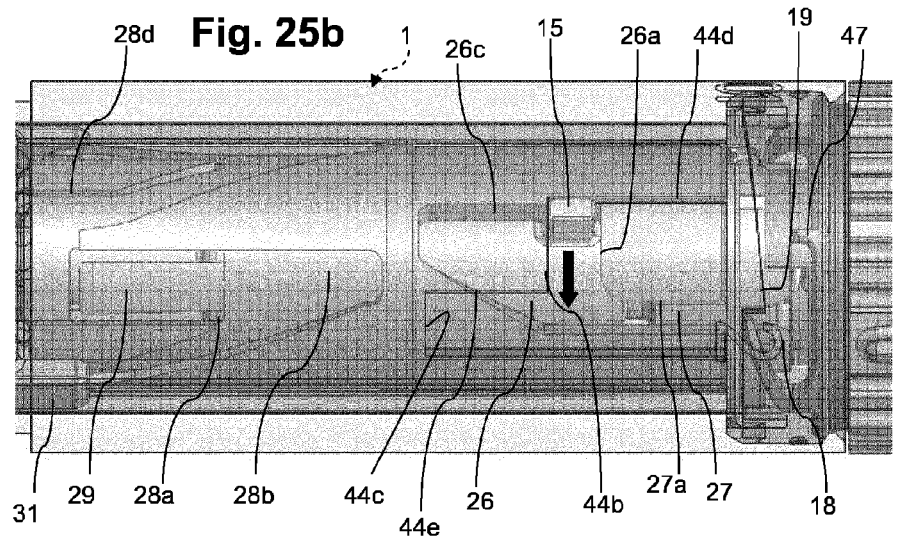
FIGS. 26a, 26b and 26c show the steps of delivery of the second dose.
Figure 26B:
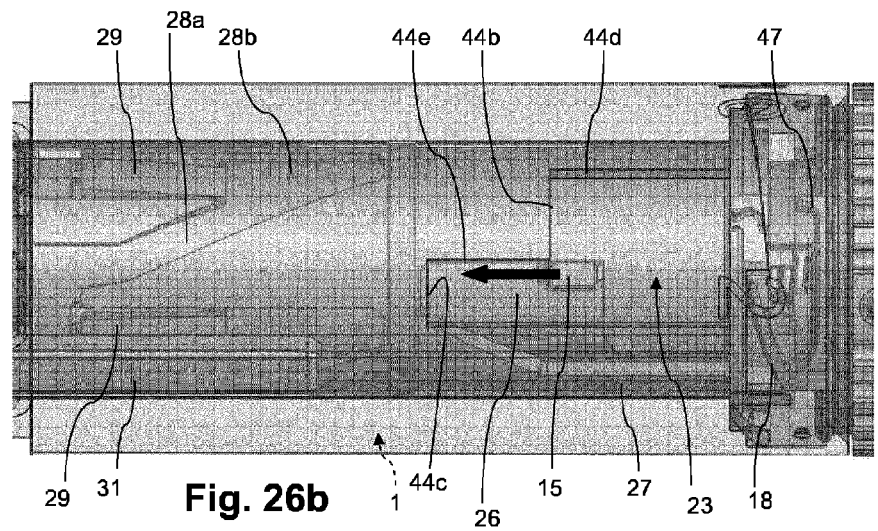
Figure 26C:
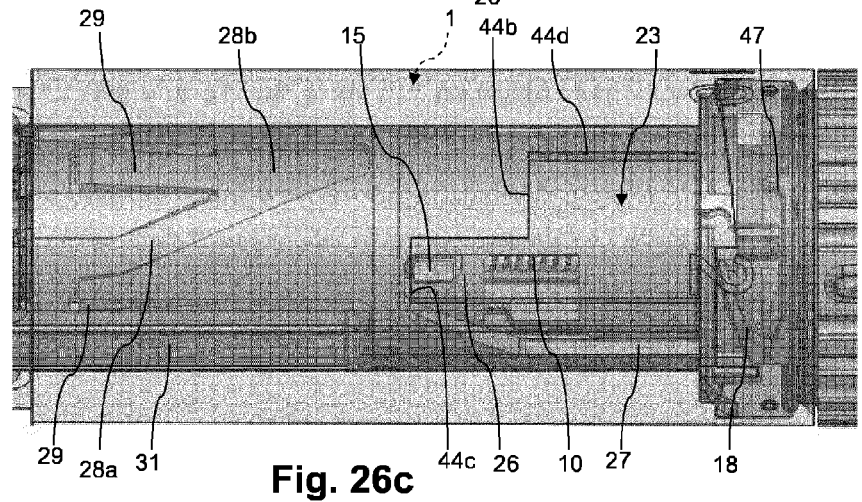
Figure 27:
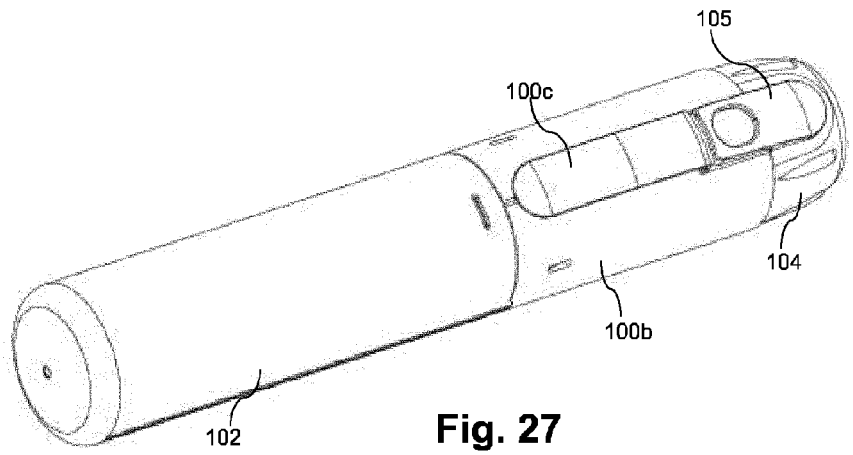
FIG. 27 is a perspective assembly view of a second embodiment of the autoinjector device according to the present invention.
Figure 28:
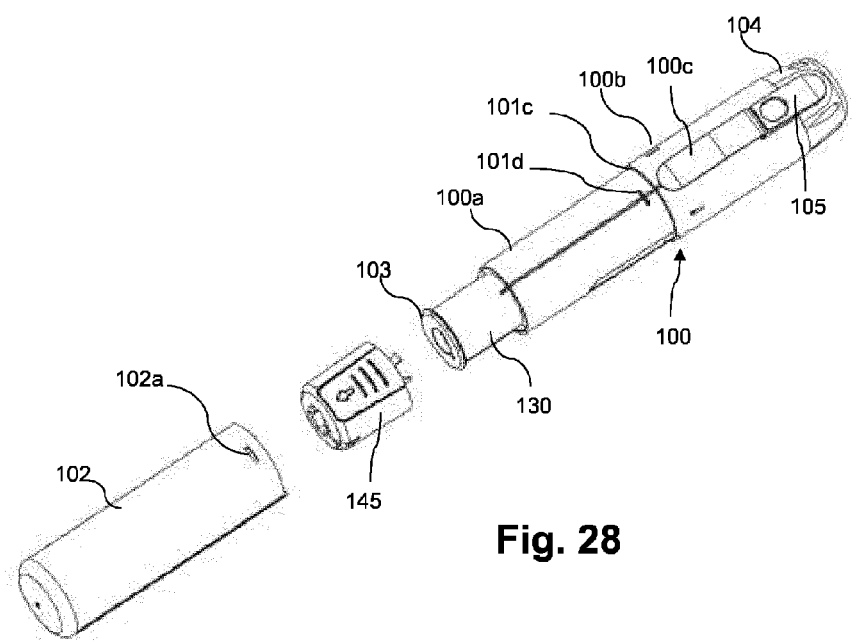
FIG. 28 is a perspective partially exploded view of the device of FIG. 27.
Figure 29:
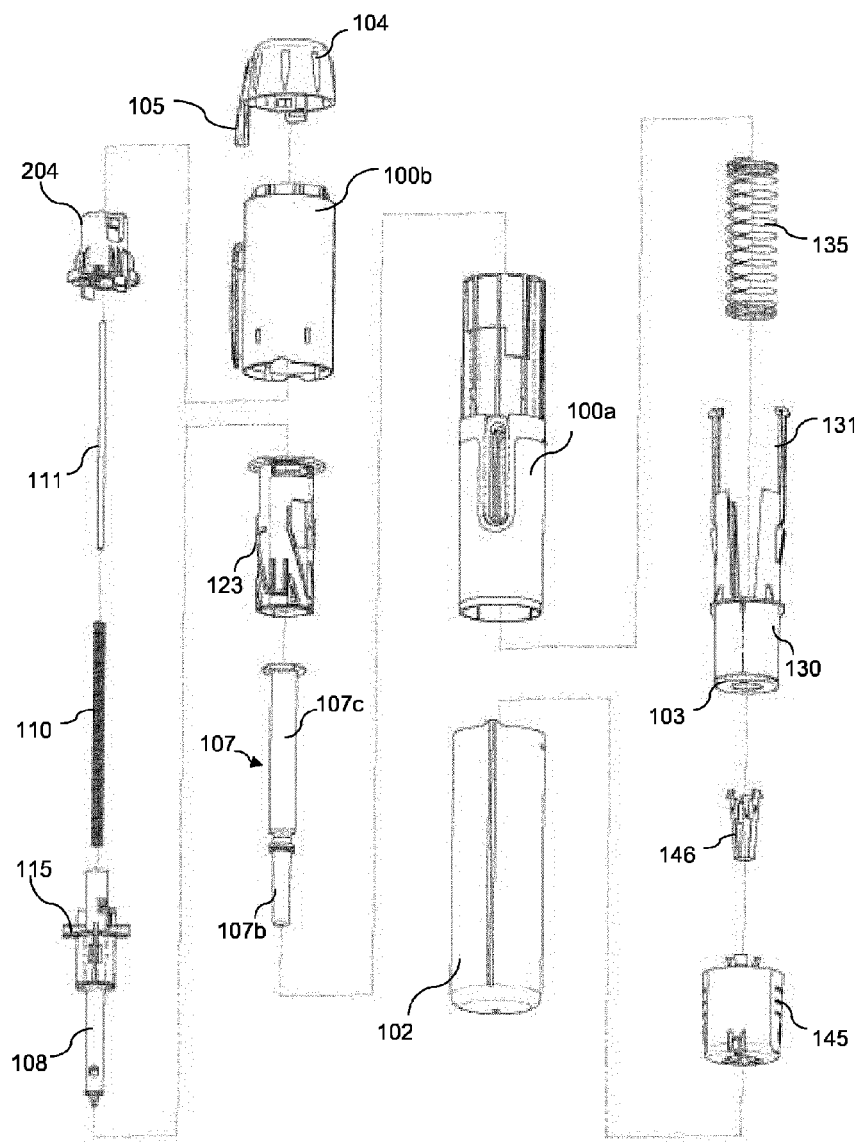
FIG. 29 is a fully exploded view of the device of FIG. 27.

While the cam sleeve 23 keeps on rotating, the radial pegs 15 slide on the second location face 44b of the stepped guide 44 as pushed by the axial side 26c of the window 26 until they reach the end of said face, from which they fall off the stop ledge 44c of the stepped guide 44 due to the action of the power spring 10. This operating sequence is shown in FIGS. 26a and 26b. The resulting axial sliding of the plunger rod 8 causes the second dose to be delivered.

It is worth noting that a small drug volume always remains in the syringe barrel. In fact, the position of the stop ledge 44c of the stepped guide 44 is designed in the way that, when the radial pegs 15 reach the stop ledge 44c, the plunger stopper 7d does not touch the bottom of the barrel 7c. In this way, not only the delivery of the prescribed volume of drug is allowed to be controlled, but also any manufacturing variability with respect to the internal length of the syringe barrel is ensured to be mitigated. Therefore the dose accuracy is improved.

After delivery of the second dose, the user removes the device from the injection site and the needle 7a withdraws therefrom. The return spring 35 is no longer hindered by the forced contact between the front end 3 and the injection site and thereby pushes the slidable sheath 30 axially forward thus resheathing the needle. At the same time the drive pins 32 of the drive legs 31 slide down in the downward track 28b of the drive cam means 28 and depress inwardly the cantilever legs 29 until the device returns to a "lock-out" condition, wherein the drive pins 32 contact the free end 29a of the cantilever legs 29 and the assembly clips 39 of the sliding sheath 30 again engage with end stops 40 of the outer body 1, as at the end of the delivery of the first dose. The needle 7a is again not accessible as being covered by the sliding sheath 30. The user then recaps the device with its end cap 2 before disposal/handling to paramedic.

Even if the autoinjector device according to the invention described above is equipped with two radial pegs 15 to guide the movements of the plunger rod 8, this solution being the preferred one to have a symmetrical distribution of the forces acting on the various components, it is clear that the solution in which only one radial peg 15 is provided is comprised in the scope of the invention as being an obvious variation thereof. In this case, the stepped guide means 44, the trigger cam means 26, 27 and the drive cam means 28 will be modified consequently.

FIGS. 27 to 48 show a second embodiment of the autoinjector device according to the invention featured by a different configuration of some components, while maintaining a substantially equal operation relative to the autoinjector device described above.

With reference to FIGS. 27-31, in the autoinjector device according to the second embodiment of the present invention the outer body, generally indicated at 100, is formed by two distinct components 100a and 100b, called chassis and outer sleeve respectively, which can be secured to each other coaxially. In particular, a portion of the chassis 100a engages within sleeve 100b and is secured thereto by teeth 101a snap fitting in corresponding grooves 101b of sleeve 100b (see FIG. 36). The outer diameter of sleeve 100b is greater than that of the chassis 100a, thus forming a step 101c, against which the end of a removable end cap 102 abuts, said cap 102 concealing the front end 103 of the device. The removable end cap 102 is removably fixed to the chassis 100a by cap retention teeth 101d snap fitting in corresponding grooves 102a formed on end cap 102. A pen-type clip 100c extends along the side wall of sleeve 100b to hang the autoinjector device, for example, to a pocket.

In the proximity of the other end, the rear end, of the outer body 100 angularly spaced reference marks are formed or labelled, for example the numerals 0, 1, 2, indicating a rest or stored state (0), and two operating states (1, 2) of the device, as will be explained later on.

A dose selection knob 104, from which a reference indicator 105 axially extends, is provided at the rear end of the outer body 100. The dose selection knob 104 is axially pivotable relative to the outer body 100 to allow the indicator 105 to align to the reference marks formed thereon.

In the present embodiment of the invention a substantially cup-shaped ratchet 204 is housed underneath the dose selection knob 104. The ratchet 204 is made integral to knob 104 through a pair of wings 205 internally extending in the knob at diametrically opposite parts and formed with cuts 206 for snap fitting with side axial retention ribs 204c of the ratchet 204 (see FIGS. 32 and 33).

A syringe group, generally indicated at 106, is housed in the outer body 100. As shown in FIG. 39 the syringe group comprises a drug preloaded syringe 107, with needle 107a, needle shield 107b (see also FIG. 29), barrel 107c and inner plunger stopper 107d. In the barrel 107c there engages the end of a plunger rod 108, formed by a tubular element in two parts, front part 108a and back part 108b of different outer diameter. The front part 108a has a cross section that is in a clearance condition with respect to the inner section of the barrel 107c so that it can slide therein, and an end configured for engagement with the plunger stopper 107d as a result of an axial movement to push it forward on drug delivery. The back part 108b of the plunger rod 108 has a larger diametrical size.

The inner diameter of the plunger rod 108 is sized to house a power spring 110 axially extending all over its length. As shown in FIGS. 30 and 31, the power spring 110 is in a compressed state and abuts against the closed end of the front part 108a of the plunger rod 108 with one end and against a bottom wall 204a of the ratchet 204 with its other end. The power spring 110 also winds up around a support rod 111 extending from a retention hole 204b centrally formed in the bottom wall 204a of the ratchet 204 up to the closed end of the front part 108a of the plunger rod 108. The arrangement of the power spring 110 between the support rod 111 and the inner wall of the front part 108a of the plunger rod helps to minimize buckling of the power spring 110.

From the bottom wall of the dose selection knob 104 there extend inwardly a pair of diametrically opposed bosses 109 (FIG. 35) configured to engage with corresponding cut-outs 207 formed on the bottom of the ratchet 204, whereby a rotational torque exerted by the user on the dose selection knob 104 is transferred to the ratchet 204 through the bosses 109 and the cut-outs 207 and from the ratchet 204 to the autoinjector device components connected thereto, as will be explained herebelow.

Figure 33:
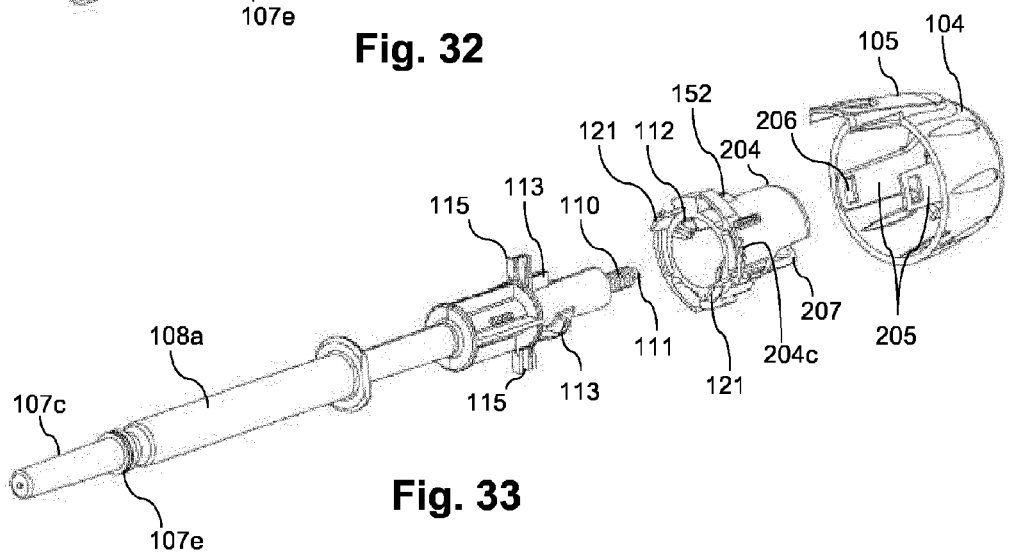
FIG. 33 is an exploded view of the detail of FIG. 32.
Figure 33A:
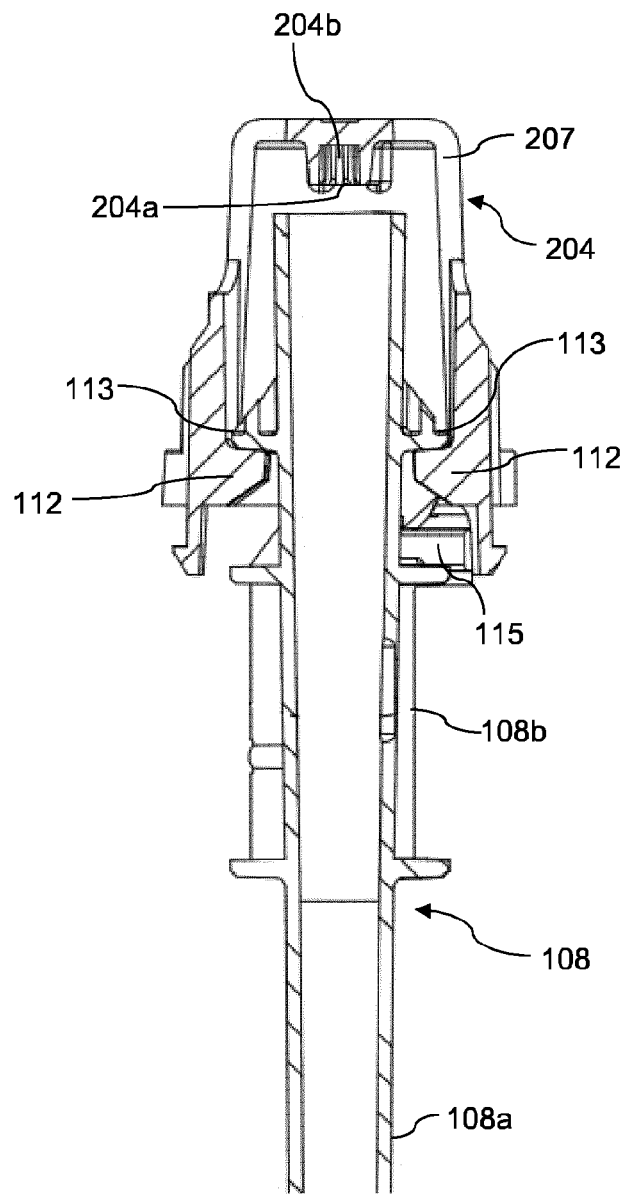
FIG. 33a is a detail sectional view of the connection between plunger rod and ratchet.
Figure 34:
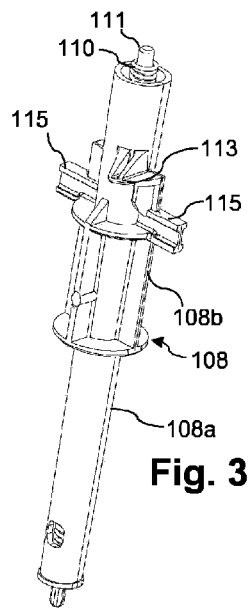
FIG. 34 is a top perspective partial view of the plunger rod.
Figure 35:
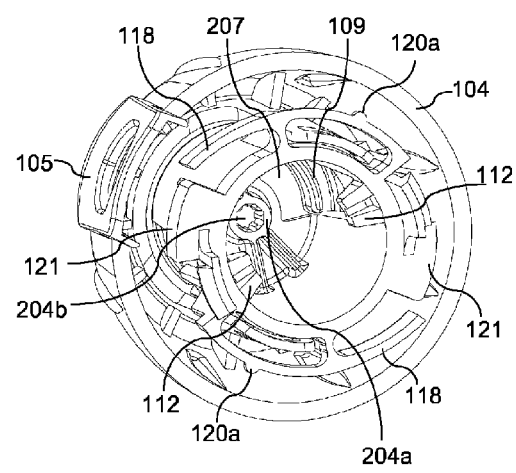
FIG. 35 is an axial perspective view of the dose selection knob-ratchet assembly.
Figure 36:
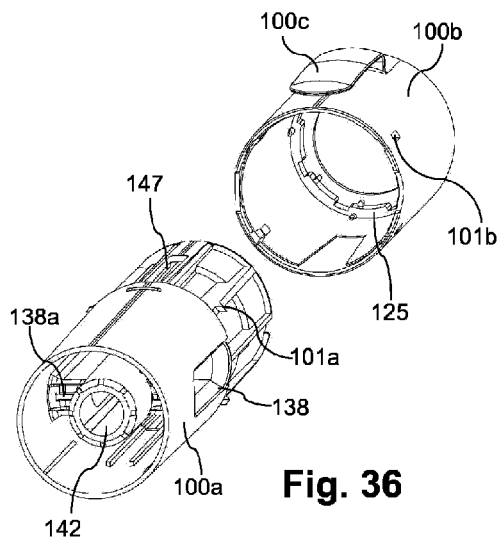
FIG. 36 is an exploded perspective view of the chassis-outer sleeve assembly forming the outer body of the device of FIG. 27.

The plunger rod 108 and the ratchet 204 are coupled by a bayonet connection that keeps the power spring in a compressed state until the device is triggered. With reference to FIGS. 33 to 35, the bayonet connection comprises a pair of retention feet 112 inwardly projecting from the ratchet 204 at diametrically opposed parts and corresponding actuation slots 113 extending from the plunger rod 108 and hanging on the retention feet 112. The holding stability is ensured by axial force provided by the compressed power spring 110, but the connection does not have any circumferential constraints other than that due to the mutual friction between feet 112 and slots 113.

Figure 32:
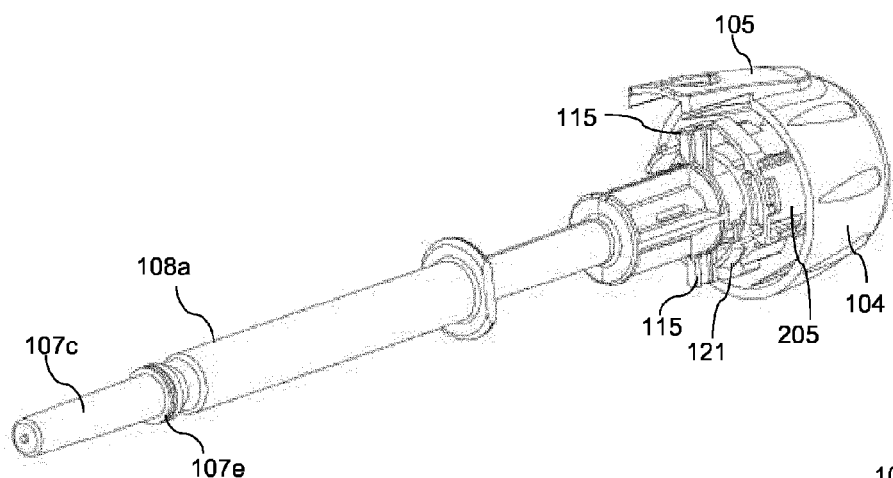
FIG. 32 is a detail view of the connection between the dose selection knob and the plunger rod in the device of FIG. 27.

Two radial pegs 115 outwardly project from the rear part 108b of the plunger rod 108 at diametrically opposed parts. The two radial pegs 115, shown in particular in FIGS. 32-34, provide a means to guide the movement of the plunger rod 108, which controls the drug dose delivery, by sliding in trigger cam means, as will be explained later on.

The connection between the outer sleeve 100b and the knob-ratchet assembly is made (see FIGS. 30 and 31) through an inwardly facing flange 150 of the sleeve 100b abutting on a running rim 151 of the ratchet 204, while the free edge of the knob 104 abuts on the rear edge of the outer sleeve 100b. In this way the sleeve 100b is held captive between the selection knob 104 and the ratchet 204 during the snapping together process. Centering ribs 152 extend from the running rim 151 on the ratchet 204 to provide axial alignment between the ratchet 204 and the sleeve 100b.

The dose selection knob 104 may rotate in only one direction relative to sleeve 100b and to this end the connection between the ratchet 204 and the sleeve 100b comprises means for preventing the rotation in the direction opposite to that of dose selection after the knob reaches one of the operating positions. These means comprise a pair of flexible ratchet legs 118 (see FIGS. 35 and 36) perimetrically extending from the edge of the ratchet 204, suited to slidably abut, when the knob 104 is rotated, on respective anti-back-rotation ribs 119, visible in FIG. 43c, of the sleeve 100b. When the legs 118 slide, first they flex due to the presence of ribs 119 and then, once the ribs have overcome, they trigger abutting against it and preventing the reverse rotation of knob 104. A stop rib 120 (visible in FIG. 43c) is also provided along the face of the sleeve 100b on which the ratchet 204 slides. A corresponding protrusion 120a of the ratchet 204 abuts against the stop rib 120 to prevent any further knob forward rotation after the knob reaches the position corresponding to the dose delivery. However, the protrusion 120a must deflect, as a result of a moderate force, to overcome the stop rib 120 and allow the passage from an operating position to the other.

Figure 41A:
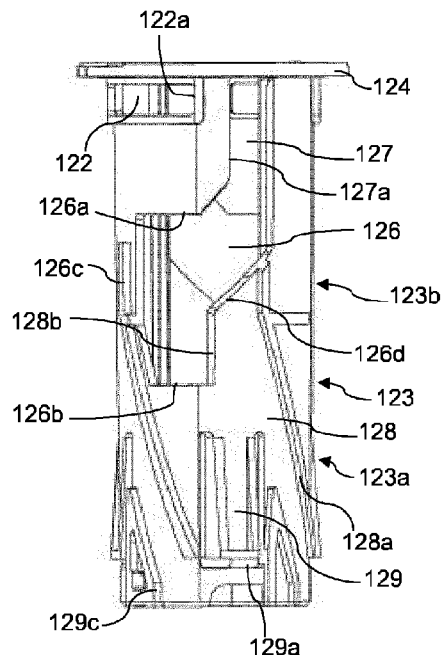
FIGS. 41a, b and c are, respectively, side view, perspective view and reversed perspective view of the cam sleeve in the device of FIG. 27.

As shown in FIGS. 33 and 41a,b,c, a pair of diametrically opposed feet 121 axially extend from the ratchet 204 over the part 108b of the plunger rod 108 and engage in respective grooves 122 of a support 123 of tubular shape, referred to as cam sleeve 123 in the present description, formed at the rear end thereof. The grooves 122 have a leading edge 122a against which a turning leg 121a of the feet 121 abut to bring the cam sleeve 123 into rotation integrally with the dose selection knob 104 through the ratchet 204. A positioning flange 124 (see also FIGS. 30 and 31) outwardly extend around the same end of the cam sleeve 123 designed to rest with one face on a corresponding rim 125 within the outer sleeve 100b near its rear end, and with the other face on the back edge of the chassis 100a, thereby preventing the mutual axial sliding.

Figure 41B:
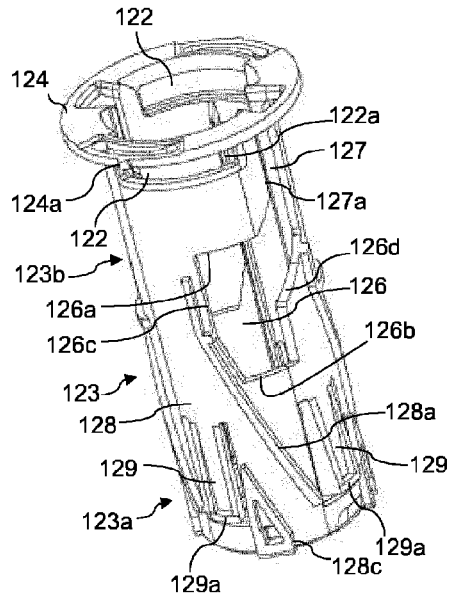
Figure 41C:
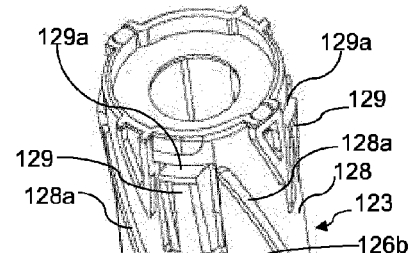

As shown in FIGS. 41a, 41b and 41c, the cam sleeve 123 is formed with two sections with different functions: a first section 123a toward the front end of the device, called front section, and a second section 123b toward the rear end, called rear section. The front section 123a is operatively connected to a slidable sheath 130 (see FIG. 30), whose axial sliding causes the cam sleeve 123 to displace angularly, as will be explained later on, while the rear section 123b is operatively connected to the radial pegs 115 of the plunger rod 108 and, as already said, to the dose selection knob 104 (see especially FIG. 42) through the ratchet 204.

The cam sleeve 123 is pivotable in the outer sleeve 100b and is kept into axial alignment by the positioning flange 124. The rotation stop end is made by a pair of side ribs 124a on the outer edge of flange 124 abutting on corresponding abutments, not shown, formed in the sleeve 100b.

The rear section 123b of the cam sleeve 123 is provided with trigger cam means to control the movements of the plunger rod 108. The trigger cam means comprise two windows 126 diametrically opposed and symmetrical to the axial rotation as regard their shape, opened toward the rear edge of the cam sleeve through a respective axially extending channel 127 defining a first dose trigger cam track 127a. Each window 126 is delimited by two parallel circumferential sides 126a and 126b, by an axial side 126c linking two ends of the sides 126a, 126b, and by an inclined side 126d, opposed to the axial side 126c, linking the other end of the side 126b, opposite to the channel 127, to one side of the channel 127. The channel 127 opens in the window 126 at the inclined side 126d and the axial side 126c forms the second dose trigger cam track. The first dose trigger cam track 127a is angularly spaced from the second dose trigger cam track 126c. In the present embodiment the side 126b is placed at the end of a widened gap in windows 126 to account for clearances and tolerances associated with manufacturing variation of component features.

Drive cam means 128 are embossed on the outer surface of the front section 123a of the cam sleeve 123. The drive cam means 128 is formed by a cam profile repeated four times in an angularly equispaced fashion on said surface. The cam profile comprises a first drive cam track 128a, extending from the end of the cam sleeve 123, called upward track for sake of simplicity, and inclined with respect to the axis X, and a second drive cam track 128b, called downward track for sake of simplicity, extending from the same end of the cam sleeve 123 and incident with the first drive cam track 128a. On the upward track 128a and, successively, on the downward track 128b a pair of drive pins 132 is designed to slidingly urge. The drive pins 132 project inwardly from two diametrically opposed, axial drive legs 131 of the sliding sheath 130 (FIGS. 40a, 40b and 40c). Sliding occurs when a pressure action is exerted on the free end 103 of the sliding sheath 130, whereby the cam sleeve 123 is rotated in the opposite direction to the inclination direction of the upward track 128a, and, respectively, when the pressure action ceases.

In the downward track 128b of the drive cam means 128 relevant cantilever legs 129 are formed to be inwardly deflected to allow passage of the drive pins 132 during the drive pin return stroke in the downward track. In the stored state of the device the drive pins 132 abut on an axial lock-out edge 129a at the free end of the cantilever legs 129, thereby preventing the sliding sheath 130 from moving toward the rear end of the device. A stop edge 128c, placed sideways of the axial lock-out edge 129a, serves as abutment for drive pins 132 to prevent the ratchet 204 from rotating beyond the positions of first dose and second dose delivery, as will be explained later on.

The end of the sliding sheath 130 at the side opposite to the drive legs 131 constitutes the front end 103 of the device, i.e. the end intended to be brought into contact with the patient skin at the injection site. The needle 107a of the syringe 107 will project from said front end 103 through a central aperture 133 thereon. A return spring 135 abuts with one end against the inner face of the front end 103 of the sliding sheath 130 and against pushing surface of chassis 100a with its other end. Sideways the return spring 135 is guided by alignment ribs 134 formed inside the sheath 130.

A pair of assembly clips 139 extends outwardly from the ends of the legs 131 to snap engage with axial guide slots 147 formed along the chassis 100a. The legs 131 deflect when the device is being assembled so as to allow the assembly clips 139 to engage in the slots 147 and the axial movement of the sliding sheath 130 while preventing release thereof.

Since the drive legs 131 are slidingly engaged with axial guide slots 147 formed in the chassis 100a, the sliding sheath 130 may only move axially in the outer body 100 along axial alignment tracks 136 inwardly projecting from the inner face of the chassis 100a. Two wide axial openings 137, arranged at 90° relative to drive legs 131, are formed on sliding sheath 130. The axial openings 137 are axially aligned to corresponding transparent inspection windows 138 formed on the chassis 100a, through which the barrel 107c of the syringe 107 is visible, whereby the user can control the drug delivery condition. The abutment surface for the return spring 135 on the chassis 100a is constituted by the bottom wall 138a of said inspection windows 138. The axial openings 137 allow the sliding sheath 130 to travel axially by the required distance whilst not clashing with the windows 138 of the chassis 100a.

Flexible tines 141 project from diametrically opposed parts of the sliding sheath 130 and have an active surface inclined so as to provide resistance to the movement of the sliding sheath 130 when it abuts against corresponding inner protrusions 141a at the front end of the axial alignment tracks 136 of the chassis 100a (see FIGS. 30 and 37) and make this movement possible only as a result of a moderate thrust that deflects the tines 141 inwardly to overcome the protrusions 141a. The motion subsequently created by the release of the tines 141 helps to quickly insert the needle 107a of the syringe 107 into the injection site.

A tubular housing 142 for the syringe 107 is formed in the chassis 100a and an inward edge 142a is formed at the front end thereof, on which the front end of the barrel 107c seats. At the other end of the tubular housing 142 the barrel 107c projects with a flange 107e, above which the front face of the cam sleeve 123 lies (see FIGS. 30 and 31).

Figure 37:
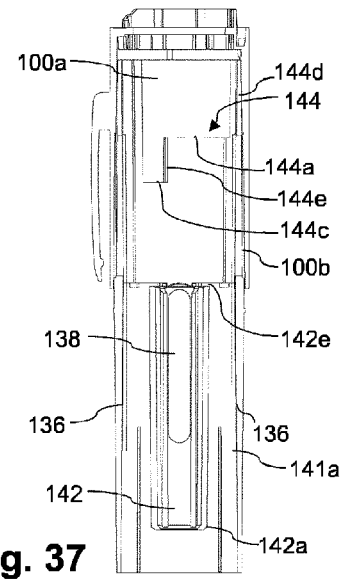
FIG. 37 is a longitudinal section of the chassis-outer sleeve assembly of FIG. 36 as assembled.

As shown in FIG. 37, guide means 144 for the radial pegs 115 are embossed on the inner surface of the chassis 100a to control the axial movement of the plunger rod 108 and limit in this way the volume of drug delivered. These guide means are in the form of a stepped track with a location face 144a and a stop ledge 144c, lying on planes perpendicular to the axis X. The edge of the location face 144a is connected to the rear edge of the chassis 100a by a first axial side 144d and to the stop ledge 144c by a second axial side 144e. A pair of diametrically opposed stepped tracks, symmetrical to the axial rotation as regards their shape, are formed on the inner face of the chassis 100a. The radial pegs 115 of the plunger rod 108 are designed to jump down from a position at the rear of the chassis 100a, whereby the relative axial position of the pegs 115 is defined by the connection of the bayonet feature between retention feet 113 and actuation slots 112, onto the location face 144a at the first dose delivery, and to slide on it as a result of the rotation of the cam sleeve 123, finally falling off from the location face 144a to the stop ledge 144c on delivering the second dose of drug, while moving along the first axial side 144d and, respectively, the second axial side 144e, as will be explained later on.

A needle shield remover 145 is removably secured to the sliding sheath 130 by snap engageable retention fingers 145a abutting against a flange at the front end of the sheath 130 and is provided with an inner tubular grip member 145b in which an insert 146 is arranged for engaging on the needle shield 107b through retention hooks (not shown) digging into the rubber needle shield, in such a way that, by pulling the needle shield remover 145 before the first dose is administered, the user can remove the needle shield 107b and free the needle 107a for the injection.

The operation of the auto-injector device according to the second embodiment of the invention is described here below. As already said, the operation is substantially equal to that of the previously described embodiment of the invention. Reference is made to FIGS. 42 to 48 hidden line 149, where present, in these figures indicates the position of the front end of chassis 100a.

In the initial state, the stored state, the power spring 110 is compressed between the closed end of the part 108a of the plunger rod 108 and the bottom wall 204a of the ratchet 204 integral to the dose selection knob 104. The bayonet connection between the ratchet 204 and the plunger rod 108 secures the power spring 110 in compression until the first dose is triggered. Any buckling of the power spring 110 is prevented thanks to its being arranged between the part 108b of the plunger rod 108 and the support rod 111.

The needle shield 107b is secured to the syringe 107 and the needle shield remover 145 is secured to the needle shield 107b through the insert 146. The cap 102 is secured to the chassis 100a and the sliding sheath 130 is prevented from moving axially because the drive pins 132 of the drive legs 131 abut against the respective lock-out edges 129a of the cam sleeve 123.

The dose selection knob 104 is connected to the outer body 100 as the sleeve 100b is held captive between the knob 104 and the ratchet 204 integral to each other. Once assembled, the assembly formed by the dose selection knob 104 and the ratchet 204 cannot move axially, but can only rotate in one direction. The rotation direction is indicated by the reference marks on the outer body 100: in other words, indicator 105 starts from the position 1, rotates to the position 1 when the first dose is selected, and then rotates to the position 2 when the second dose is selected.

In the stored state the device is "locked-out", i.e. the sliding sheath 130 cannot move in the outer body 100, because the drive legs 131 of the sliding sheath 130 abut against the axial lock-out edges 129a of the cam sleeve 123. This condition is shown in particular in FIGS. 42 e 43a. On selecting the first dose (position 1), the device is unlocked as shown in 43b. As a matter of fact, by rotating the dose selection knob 104 the cam sleeve 123 is pushed in the same direction by the feet 121 of the ratchet 204 that abut on the leading edge 122a of the grooves 122 of the cam sleeve 123 with their turning legs 121a. The dose selection knob 104 cannot rotate past the position 1 until the first dose is delivered, because the drive pins 132 of the legs 131 abut on the stop edge 128c of the cam track 128 on the cam sleeve 123. The slidable sheath 130 is prevented from rotating because the legs 131 can only move axially forward and backward in the axial guide slots 147 on the chassis 100a.

Figure 43C:
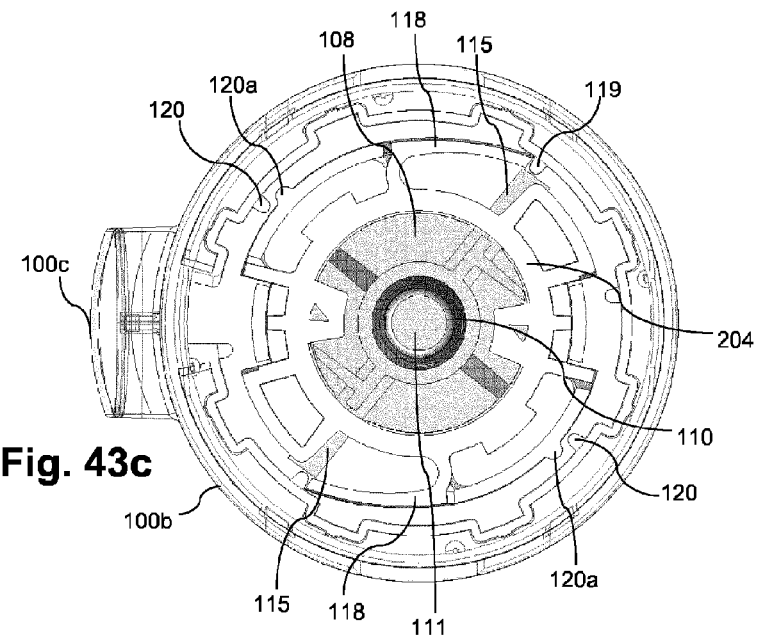
FIG. 43c is a transverse sectional view of the device in the first dose armed position of FIG. 43b.
Figure 44A:
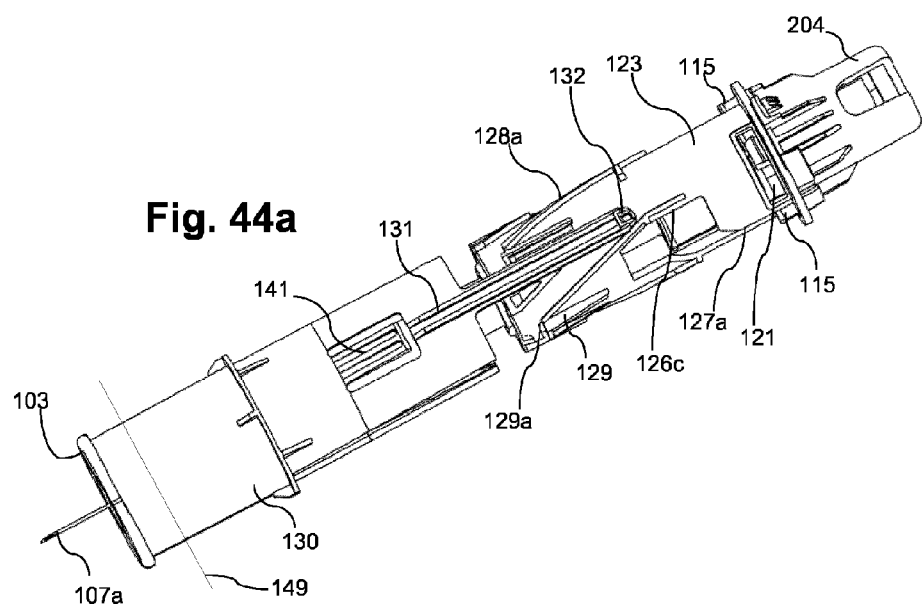
FIGS. 44a and 44b show the device immediately before and at the triggering point.
Figure 44B:
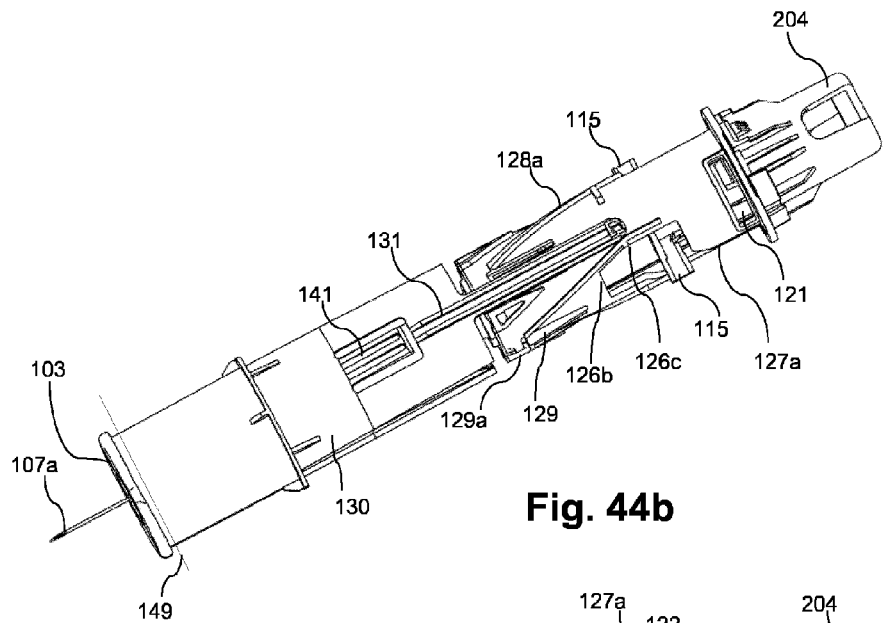

It must be pointed out that, as shown in FIG. 43a, in the rest position there is a design clearance Y between the trigger cam track 127a and the respective radial peg 115. A design clearance Z of lower extent exists between the turning legs 121a of the feet 121 of the ratchet 204 and the respective leading edges 122a of the grooves 122 of the cam sleeve 123. When the user rotates the dose selection knob 104, at the beginning he/she must overcome the resistance opposed by the stop rib 120 of the sleeve 100b abutting against the protrusion 120a of the ratchet 204 (FIG. 43c). The small rotation necessary to do this, brings the turning legs 121a into contact to the leading edges 122a, while a residual clearance still exists between the trigger cam track 127a and the respective radial peg 115.

First the user must slide back and remove the end cap 102 in order to expose the needle shield remover 145. The end cap 102 will have to be replaced once the first dose is delivered when the device is not in use. The end cap 102 protects the drug from light exposure and prevents particulates from coming into contact with the front end 103 of the device.

To perform the first injection the user must remove the needle shield remover 145. In this way the insert 146 and the needle shield 107b are also removed leaving the needle 107a uncovered, but still sub-flush of the front end 103 and not readily visible to the user. To unlock the device and select the delivery of the first dose, the user rotates the dose selection knob 104 from position 0 (stored state) to position 1 (first dose armed).

Figure 45:
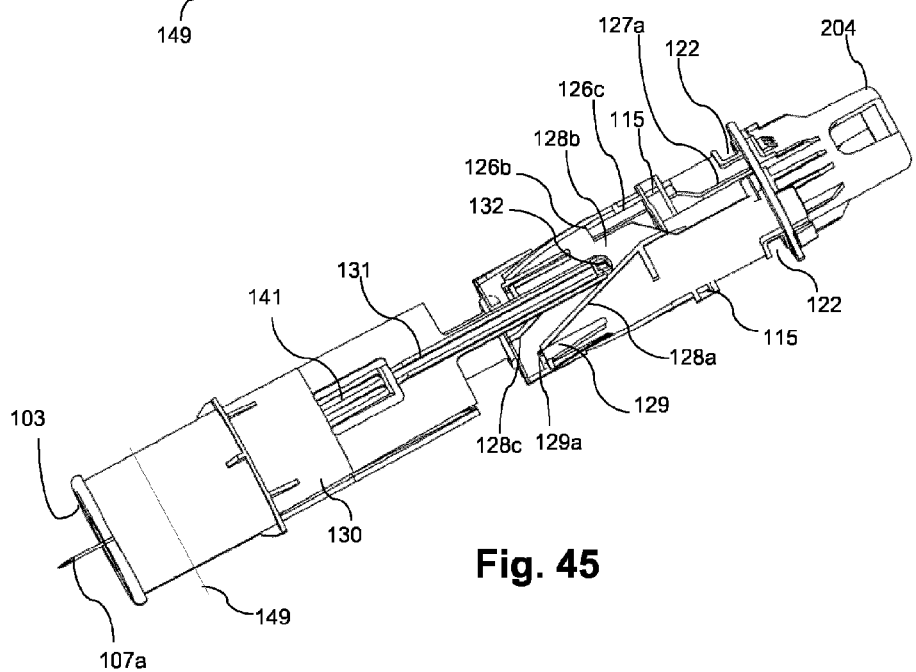
FIG. 45 shows the device after delivering the first dose during the resheating step.

The rotation of the dose selection knob 104 from position 0 to position 1 causes the rotation of the cam sleeve 123, whereby the axial lock-out edges 129a of the cantilever legs 129 displace relative to the drive pins 132 of the legs 131 of the slidable sheath 130, which abut against the stop edge 128c to prevent the knob 104 to further rotate until the first dose is delivered and are aligned to the upward portions 128a of the cam track 128 free to move along them (see FIGS. 43b and 45). The user recognizes the end of rotation to position 1 when he/she sees that the indicator 105 lines up with the position 1 marker, feels the increase in rotation resistance of the drive pins 132 contacting the cam track 128 and also hears the "click" as produced by the ratchet legs 118 clicking as a result of their falling off the relevant ribs 119. The contrast between the legs 118 and the relevant ribs 119 prevents the reverse rotation of the knob 104, whereas any forward rotation is hindered by the abutment between the stop rib 120 of the sleeve 100b and the protrusion 120a of the ratchet 204 (FIG. 43c)

The device is triggered by the user pressing the front end 103 of the sliding sheath 130 against the injection site by keeping the device through the outer body 100. The movement of the sliding sheath 130 in the outer body 100 finds a resistance due to the contrast between the flexible tines 141 of the sliding sheath 130 and the inner protrusions 141a of the chassis 100a. Due to their flexibility and the inclined contact surface, the flexible tines 141 depress and fully deflect inwardly while overcoming the protrusions 141a to allow the passage of the sliding sheath 130 which can slide in the chassis 100a leaving the needle 107a to project from its front end 103, so that the needle can penetrate in the injection site. The motion subsequently created by the release of the flexible tines 141 helps to quickly insert the needle 107a in the injection site FIG. 44a).

The axial movement of the sliding sheath 130 in the outer body 100 causes the rotation of the cam sleeve 123 and the latter would frictionally draw into rotation also the ratchet 204 and the dose selection knob 104. To prevent the knob 104 from rotating during the step of first dose delivery, between the ratchet 204 and the sleeve 100b temporary stop means are provided that mutually engage when the free ends of the ratchet legs 118 fall off the ribs 119 of the sleeve 100b. In the present embodiment the temporary stop means comprise the stop ribs 120 of the sleeve 100b abutting on the corresponding protrusions 120a of the ratchet 204, as shown in FIG. 43c. The rotational force acting on the ratchet 204 upon triggering is less than the retention force provided by the stop ribs 120. However, the rotational force that the user is able to provide is much larger than that of stop ribs 120. Therefore, the user can overcome the rib force and rotate the knob 104 to arm the device for the second dose.

The rotation of the cam sleeve 123 causes the plunger rod 108 to rotate because of its radial pegs 115, engaged in the corresponding axial channels 127 are pushed by the trigger cam track 127a. The angular displacement of the plunger rod 108 causes the bayonet connection to decouple as the actuation slots 113 of the plunger rod 108 slide on the respective retention feet 112 of the ratchet 204 until the slots 113 get free of the feet 112. This sequence is shown in FIG. 49. At this point the power spring 110, no longer retained by the bayonet connection, applies its elastic thrust on the plunger rod 108 which moves forward in the cam sleeve 123 until radial pegs 115, sliding in the axial channels 127, lean on the location face 144a of the stepped guide 144 of the sleeve 100b (see FIG. 47a). The resulting axial sliding of the plunger rod 108 causes the delivery of the first dose.

Figure 46A:
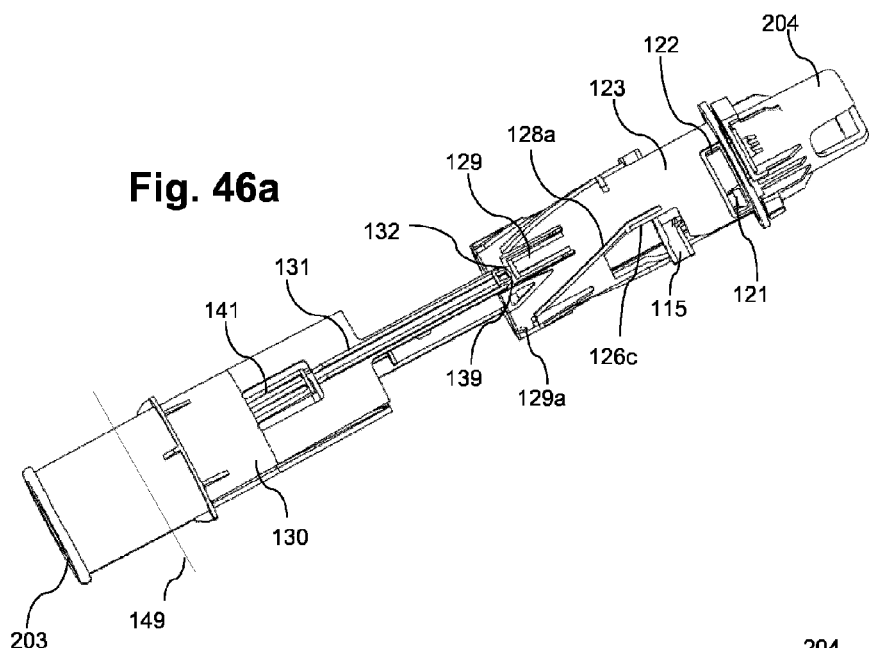
FIGS. 46a and 46b show the device in the stored position after delivering the first dose and, respectively, in the second dose armed position and ready for delivering the second dose.

After delivery of the first dose, the user removes the device from the injection site and the needle 107a withdraws therefrom. The return spring 135 is no longer hindered by the forced contact between the front end 103 and the injection site and thereby pushes the slidable sheath 130 axially forward thus resheathing the needle. At the same time the drive pins 132 of the drive legs 131 slide down in the downward portion 128b of the cam track 128 depressing inwardly the cantilever legs 129 until the device returns to a "lock-out" condition, wherein the drive pins 132 contact the free end 129a of the cantilever legs 129 and the assembly clips 139 of the sliding sheath 130 again engage with end stops 140a in the axial guides 136 of the chassis 100a, as shown in FIG. 46a The needle 107a is again not accessible as being covered by the sliding sheath 130, which, in this state, is prevented from sliding until the user rotates the dose selection knob 104 to position 2. The user then recaps the device. The end cap 102 snap fits with outer body 100 to securely hold on the chassis 100a.

If the delivery of a second dose is necessary, the user un-caps the device to enable access to the sliding sheath 130. To unlock the device the user must rotate the dose selection knob 104 from the position 1 (first dose armed position) to the position 2 (second dose armed position) (see FIGS. 46a and 46b).

Figure 46B:
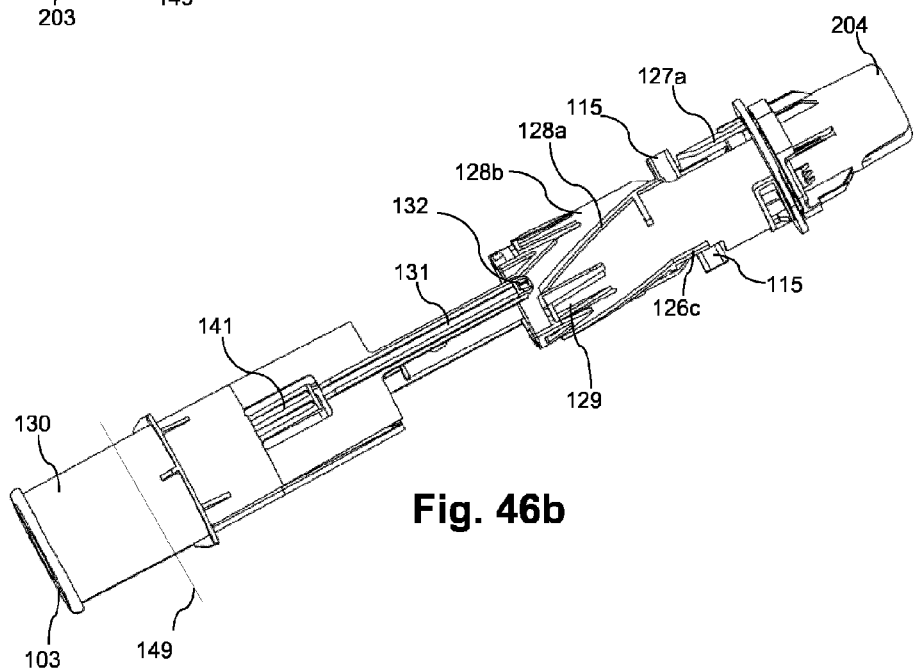
Figure 48A:
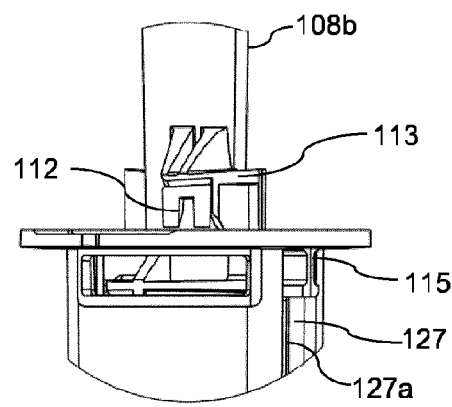
FIGS. 48a, b and c are detail side views of the bayonet connection of the device according to the second embodiment of the invention before, during and, respectively, at the decoupling step.
Figure 48B:
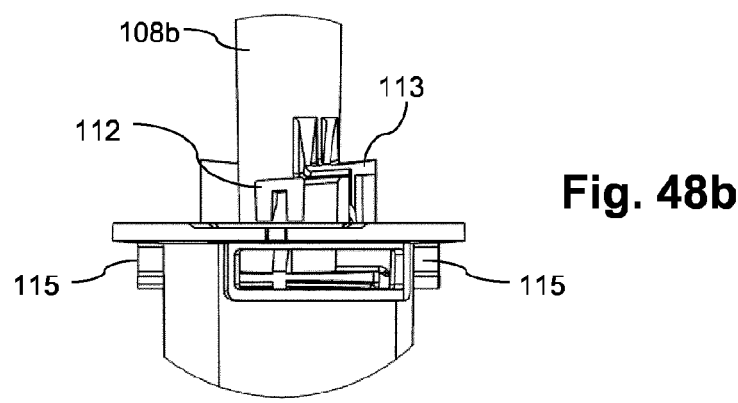
Figure 48C:
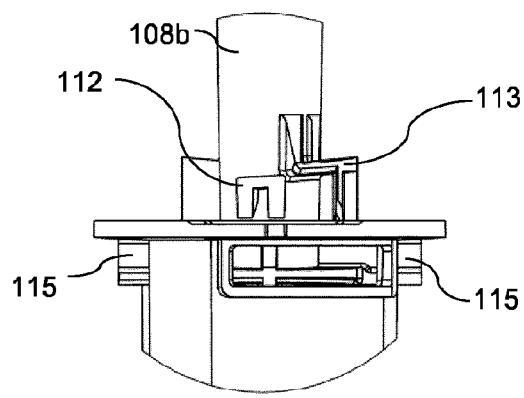

To that end the user must overcome the reaction of the stop ribs 120 of the sleeve 100b on the protrusions 120a of the ratchet 204. Deflection of protrusions 120a allows the knob 104 to rotate. The feet 121 of the ratchet 204 take up the free travel on grooves 122 of the cam sleeve 123 until the turning legs 121a reach the leading edges 122a to rotate the cam sleeve 123 to position 2, as shown in FIGS. 46a and 46b. In this case too, reaching the position 2 is announced by a click as for the position 1.

The rotation of the cam sleeve 123 causes the device to unlock because the drive pins 132 of the drive legs 131 of the sliding sheath 130 line up the upward portion 128a of the cam track 128 while contacting the stop edge 128c to prevent a further rotation of the knob 104 once the position 2 is reached. The reverse rotation of the dose selection knob 104 is prevented by the ratchet legs 118 snap abutting on the protrusions 119 of the sleeve 100b. The rotation of the cam sleeve 123 also causes the repositioning of the radial pegs 115 from the outlet of the axial channel 127 within the window 126 to the opposite axial side 126c, while their position on the location face 144a of the stepped guide 144 is unchanged (FIGS. 46b and 47a).

The device is triggered for the delivery of the second dose by the user pressing the front end 103 of the sliding sheath 130 against the injection site by keeping the device through the outer body 100. The movement of the sliding sheath 130 in the chassis 100a caused by the drive pins 132 of the legs 131 pushing against the upward track 128a finds a resistance due to the contrast between the flexible tines 141 of the sliding sheath 130 and the inner protrusions 141a of the chassis 100a. Due to their flexibility and the inclined contact surface, the flexible tines 141 depress and fully deflect inwardly overcoming the protrusions 141a to allow the passage of the sliding sheath 130 which can slide in the chassis 100a leaving the needle 107a to project from the front end 103, so that the needle can penetrate in the injection site. The motion subsequently created by the release of the flexible tines 141 helps to quickly insert the needle 107a into the injection site. The thrust produced by the drive pins 132 does not cause any significant axial movement of the cam sleeve 123, because its positioning flange 124 axially abuts against the rim 125 of the sleeve 100b.

To prevent any further rotation of the knob 104, once the position 2 is reached, at the end of the following rotation of the cam sleeve 123 the free end of the ratchet legs 118 abut on the stop ribs 119 thus preventing the reverse rotation of the knob 104, whereas the forward rotation is hindered by the contrast between the stop rib 120 of the sleeve 100b and the protrusion 120a of the ratchet 204 (FIG. 43c).

While the cam sleeve 123 keeps on rotating, the radial pegs 115 slide on the location face 144a of the stepped guide 144 as pushed by the axial side 126c of the window 126 until they reach the end of said face, from which they fall off the stop ledge 144c of the stepped guide 144 due to the action of the power spring 110. This operating sequence is shown in FIGS. 47a to 47c. The resulting axial sliding of the plunger rod 108 causes the second dose to be delivered.

After delivery of the second dose, the user removes the device from the injection site and the needle 107a withdraws therefrom. The return spring 135 is no longer hindered by the forced contact between the front end 103 and the injection site and thereby pushes the slidable sheath 130 axially forward thus resheathing the needle. At the same time the drive pins 132 of the drive legs 131 slide down in the downward track 128b of the drive cam means 128 and depress inwardly the cantilever legs 129 until the device returns to a "lock-out" condition, wherein the drive pins 132 contact the free end 129a of the cantilever legs 129 and the assembly clips 139 of the sliding sheath 130 again engage with end stops 140a in the axial guides 136 of the chassis 100a, as at the end of the delivery of the first dose. The needle 107a is again not accessible as being covered by the sliding sheath 130. The user then recaps the device with its end cap 102 before disposal/handling to paramedic.

The autoinjector device according to the invention is suitable to the delivery of medicaments in solution, especially epinephrine (also known as adrenaline).

In particular, the doses of epinephrine that can be administered with the device of the invention are preferably in the range of 0.05 mg to 0.5 mg for each delivered dose (from 0.1 mg to 1 mg if two doses are considered).

Preferred doses for each delivery are 0.05 mg, 0.10 mg, 0.15 mg, 0.30 mg and 0.50 mg.

The above doses are based on a concentration of the epinephrine solution preferably ranging from 0.05 mg/ml to 0.5 mg/ml, the concentrations 0.05 mg/ml, 0.1 mg/ml, 0.16 mg/ml, 0.3 mg/ml and 0.5 mg/ml being particularly preferred.

The invention claimed is:

1. An automatic drug injection device comprising:
an outer body extending along a longitudinal axis;
a syringe group placed in said outer body and fixed thereto, said syringe group comprising a syringe containing a drug to be injected, a needle and plunger means axially slidable and pivotable relative to said outer body;
means for arming said device from a stored position to a first armed position for injecting a first dose and at least a second armed position for injecting a second dose, said arming means being arranged at one end of the outer body;
first elastic means arranged between said arming means and said plunger means, said first elastic means being in compressed condition when the device is in its stored position and decompressing to push forward said plunger means and delivery successively said first dose and said at least second dose;
a sliding sheath arranged at the other end of said outer body and constrained to slide axially thereinto, as a result of a pressure exerted on its free end, in contrast with second elastic means arranged between said sliding sheath and said outer body, between a sliding lock-out position, in which said sliding sheath projects from said outer body covering the needle of the syringe, and a device trigger position, in which said sliding sheath is retracted in said outer body leaving the needle of the syringe exposed, said second elastic means being suitable to bring said sliding sheath back to said lock-out position when said pressure action ceases;
cam drive means operatively connected to said sliding sheath and axially pivotable in said outer body;
trigger cam means pivotable integrally with said cam drive means and connected operatively with said plunger means to angularly displace said plunger means to said device trigger positions of the first dose and the at least second dose, and stepped guide means integral to said outer body and operatively connected with said plunger means to control an extent of the axial sliding of said plunger means and therefore limit a volume of drug delivered for each dose, said trigger cam means and said cam drive means being formed on a same support pivotally arranged between said outer body and said plunger means.

2. The device according to claim 1, wherein said trigger cam means are formed on the outer surface of said support and comprise at least an axial slot extending from an end edge of said support and defining an axial first trigger cam track for pushing said plunger means, and at least a corresponding axial second trigger cam track for pushing said plunger means angularly spaced with respect to said first trigger cam track.

3. The device according to claim 2, wherein said stepped guide means comprises location surfaces for said plunger means lying on planes perpendicular to said axis, said plunger means being angularly displaced as a result of pushing action exerted by said trigger cam tracks along said location surfaces and then axially displaced once the end of said location surfaces is reached.

4. The device according to claim 3, wherein said stepped guide means comprise at least a stepped guide profile comprising two location surfaces and a stop ledge connected by two axial profile portions.

5. The device according to claim 3, wherein said stepped guide means are formed on an inner face of said outer body.

6. The device according to claim 1, wherein said plunger means comprise at least a radial peg outwardly extending perpendicularly to said axis to interact with said trigger cam means and said stepped guide means.

7. The device according to claim 6, wherein said plunger means comprise at least a pair of radial pegs extending at diametrically opposed parts.

8. The device according to claim 1, wherein said sliding sheath interacts with said cam drive means through free ends of axial legs extending from said sliding sheath.

9. The device according to claim 8, wherein said cam drive means are formed on the outer surface of said support and comprise, for each of said axial legs, at least a first drive cam track extending from the other end of said support and inclined with respect to said axis, and at least a second drive cam track extending from the same end of said support and incident with said first drive cam track, the free ends of said axial legs slidingly engaging with said first drive cam track and successively said second drive cam track when a pressure action is exerted on the free end of the sliding sheath, whereby said support is rotated in a direction opposite to an inclination of said first drive cam track, and respectively when said pressure action ceases.

10. The device according to claim 1, wherein said device arming means comprise a dose selection knob pivotally connected to said outer body in a way to be allowed to rotate in only one direction and temporarily connected to said support to angularly displace it to an extent able to unlock the device for the delivery of a dose.

11. The device according to claim 10, wherein said dose selection knob comprises at least two feet diametrically opposed engaged with respective slide seats of said support having a leading edge against which said feet abut to cause said support to rotate.

12. The device according to claim 10, wherein said dose selection knob is equipped with ratchet legs slidably engaged with ramp surfaces formed on said outer body, said ramp surfaces defining ramp steps against which said legs abut when said dose selection knob reaches the armed position for delivery of a dose.

13. The device according to claim 12, wherein temporary stop means are provided between the dose selection knob and the outer body for mutually engaging when free ends of the ratchet legs fall off the step of the ramp surface of the outer body.

14. The device according to claim 1, wherein said device arming means comprise a dose selection knob and a ratchet arranged within said dose selection knob and snap connected thereto, said ratchet being pivotally connected to said outer body so that it can be rotated in only one direction and temporarily connected to said support to impart it an angular displacement for unlocking the device for a dose delivery.

15. The device according to claim 14, wherein said ratchet comprises at least two feet diametrically opposed engaged with respective slide seats of said support having a leading edge against which turning legs of said feet abut to cause said support to rotate.

16. The device according to claim 15, wherein a design clearance exists between the trigger cam track and a radial peg and a design clearance of lower extent exists between the turning legs of the feet and respective leading edges of grooves of said support, whereby the rotation of the dose selection knob to arm the device for the first dose does not cause the plunger means to rotate.

17. The device according to claim 14, wherein said ratchet is equipped with flexible legs configured to slide under flexion, as a result of the rotation of the dose selection knob, on respective ribs of said outer body, and to jump abutting against them with their ends, whereby the reverse rotation of the dose selection knob is prevented when the dose selection knob reaches the armed position for delivery of a dose.

18. The device according to claim 17, wherein reversible stop means are provided between the ratchet and the outer body, for abutting against each other when free ends of flexible arms abuts against rims of said outer body.

19. The device according to claim 14, wherein a bayonet connection is provided between said arming means and said plunger means to make them axially integral in said stored position and to release them in said dose delivery operating conditions.

20. The device according to claim 19, wherein said bayonet connection comprises at least a retention clip of the dose selection knob and a corresponding substantially L-shaped slot formed by a circumferential retention slot branch and an axial release slot branch on said plunger means, in the device stored position said retention clip being engaged in said retention slot branch to oppose a thrust of said first elastic means, following to an angular displacement of said dose selection knob said retention clip sliding along said retention slot branch when passing from said stored position to said first dose delivery position until it axially lines up with said release slot branch, whereby said plunger means can move axially relative to said dose selection knob.

21. The device according to claim 19, wherein said bayonet connection comprises a pair of retention feet inwardly projecting from said ratchet at diametrically opposed parts and corresponding actuation slots extending from said plunger rod and hanging on the retention feet.

22. The device according to claim 14 wherein said outer body comprises a chassis axially engaged within an outer sleeve and integral thereto, said sliding sheath being axially slidable in said chassis, said support being axially arranged in said outer sleeve, axial legs of said sliding sheath being slidably engaged in axial slots of said chassis, said outer sleeve being connected pivotally in only one direction to said ratchet.

23. The device according to claim 22, wherein said stepped guide means are formed on an inner face of the chassis and comprise a location surface and a stop ledge connected by an axial profile portion.

24. The device according to claim 1, wherein said cam drive means comprise projecting cantilever legs capable of deflecting to allow said sliding sheath to slide with respect to said support when the pressure action on said front end ceases and to prevent sliding of said sliding sheath with respect to said support from occurring before said dose selection knob is positioned in a dose selection armed position.

25. The device according to claim 24, wherein each of said cantilever legs is arranged in a respective second drive cam track and a free end of the cantilever legs constitutes a lock-out edge against which free ends of axial legs abut when the device is in the lock-out condition.

26. The device according to claim 25, wherein a stop edge is placed sideways of said lock-out edge to serve as abutment for said ends to prevent the dose selection knob from rotating beyond the positions of first dose and second dose delivery.

27. The device according to claim 1, wherein said sliding sheath comprises flexible tines along its outer surface for abutting against a protrusion of said outer body to provide resistance to the relative axial sliding and inwardly deflect under moderate force exerted thereon through said protrusion, the elastic release of said flexible tines to the not deflected condition exerting a thrust compliant with the pressure action causing the sliding sheath to slide toward the inside of said outer body.

28. The device according to claim 1, wherein said first elastic means comprise a spring placed inside said plunger means around a support rod extending between said arming means and said plunger means.

29. The device according to claim 1, wherein said outer body is formed with at least one transparent inspection window for controlling the drug delivery condition, a corresponding axial opening axially aligned to said window being formed on said sliding sheath.

30. The device according to claim 1, wherein said needle is covered by a needle shield and a needle shield remover is removably secured to the outer body and is provided with an inner tubular grip fit for engaging with the needle shield, whereby, by pulling the needle shield remover before the first dose is administered, the user can remove the needle shield and free the needle for an injection.

31. The device according to claim 30, wherein said needle shield remover comprises an insert having hooks digging into the needle shield.

* * * * *